(12) United States Patent
Koorevaar et al.

(10) Patent No.: US 11,542,513 B2
(45) Date of Patent: Jan. 3, 2023

(54) **LETTUCE PLANTS HAVING RESISTANCE TO *NASONOVIA RIBISNIGRI* BIOTYPE NR:1**

(71) Applicant: Seminis Vegetable Seeds, Inc., St. Louis, MO (US)

(72) Inventors: Gerard N. Koorevaar, Ede (NL); Robyn L. Morgan, Fredericton, CA (US); Hieronymus J. M. van der Laan, Wageningen (NL); Vivian R. Van Oosten, Wageningen (NL); Rosa I. Weber, Wageningen (NL)

(73) Assignee: Seminis Vegetable Seeds, Inc., St. Louis, MO (US)

( * ) Notice: Subject to any disclaimer, the term of this patent is extended or adjusted under 35 U.S.C. 154(b) by 0 days.

(21) Appl. No.: 17/004,995

(22) Filed: Aug. 27, 2020

(65) Prior Publication Data

US 2021/0095298 A1   Apr. 1, 2021

Related U.S. Application Data

(60) Provisional application No. 62/906,391, filed on Sep. 26, 2019.

(51) Int. Cl.
*C12N 15/82* (2006.01)
*A01H 6/14* (2018.01)

(52) U.S. Cl.
CPC ....... *C12N 15/8209* (2013.01); *A01H 6/1472* (2018.05); *C12N 15/8286* (2013.01)

(58) Field of Classification Search
CPC .......................... C12N 15/8209; A01H 6/1472
See application file for complete search history.

(56) References Cited

U.S. PATENT DOCUMENTS

| | | | |
|---|---|---|---|
| 5,977,443 | A | 11/1999 | Jansen |
| 8,816,158 | B2 | 8/2014 | Thabuis et al. |
| 8,829,280 | B2 | 9/2014 | Thabuis et al. |
| 9,629,332 | B2 | 4/2017 | Thabuis et al. |
| 9,693,532 | B2 | 7/2017 | Thabuis et al. |
| 2006/0150283 | A1 | 7/2006 | Alexandrov et al. |
| 2007/0020621 | A1 | 1/2007 | Boukharov et al. |
| 2012/0124695 | A1* | 5/2012 | Thabuis ............... A23L 19/00 435/410 |
| 2013/0239250 | A1 | 9/2013 | Thabuis et al. |
| 2017/0318770 | A1 | 11/2017 | Schaareman et al. |

FOREIGN PATENT DOCUMENTS

| | | |
|---|---|---|
| WO | 1997046080 | 12/1997 |
| WO | 2011/058192 | 5/2011 |
| WO | 2012/065629 | 5/2012 |
| WO | 2012/066008 | 5/2012 |
| WO | 2016/066748 | 5/2016 |

OTHER PUBLICATIONS

Pelgrom et al (Recognition of lettuce downy mildew effector BLR38 in Lactuca serriola LS102 requires two unlinked loci. Molecular Plant Pathology, 240-253, Sep. 2018) (Year: 2018).*
Reyes-Chin-Wo et al (Genome assembly with in vitro proximity ligation data and whole-genome triplication in lettuce. Nature Communication, 1-11, 2016) (Year: 2016).*
Lsat_Salinas_v7—Genome—Assembly_2020—NCBI (Year: 2020).*
*Lactuca sativa* cultivar Salinas chromosome 8, whole genome shotgun seq—Nucleotide—2020_NCBI (Year: 2020).*
European Search Report and Opinion for European Appl. No. 20198280.8, dated Jan. 21, 2021.
International Search Report and Written Opinion for International Appl. No. PCT/US/2020/048706, dated Feb. 4, 2021.
Christopoulou et al, Genome-wide architecture of disease resistance genes in lettuce, G3 (Bethesda), 5 (12):2655-2669, 2015.
Cid et al., "New sources of resistance to lettuce aphids in *Lactuca* spp.," Arthropod-Plant Interactions, 6:655-669, 2012.
Hough, "Biology and Control of Currant Lettuce Aphid," Thesis: the University of Warwick, available at http://wrap.warwick.ac.uk/58268/, 2013.
McCreight "Potential sources of genetic resistance in *Lactuca* spp. to the lettuce aphid, *Nasonovia ribisnigri* (Mosely) (Homoptera: Aphididae)," HortScience, 43(5):1355-1358, 2008.
Ten Broeke et al., "Resistance to a new biotype of lettuce aphid *Nasonovia ribisnigri* in Lactuca virosa accession IVT280," Euphytica, 193:265-275, 2013.
Walley et al., "Towards new sources of resistance to the currant-lettuce aphid (*Nasonovia ribisnigri*)," Mol. Breeding, 37(4): 1-18, 2017.

* cited by examiner

*Primary Examiner* — Charles Logsdon
*Assistant Examiner* — Wayne Zhong
(74) *Attorney, Agent, or Firm* — Dentons US LLP; Alissa Eagle, Esq.

(57) ABSTRACT

Lettuce (*Lactuca sativa*) plants exhibiting resistance to *Nasonovia ribisnigri* biotype Nr:1 are provided, together with methods of producing, identifying, or selecting plants or germplasm with a *Nasonovia ribisnigri* biotype Nr:1 resistance phenotype. Such plants include lettuce plants comprising introgressed genomic regions conferring pest resistance. Compositions, including novel polymorphic markers for detecting plants comprising introgressed loci, are further provided.

26 Claims, 2 Drawing Sheets
Specification includes a Sequence Listing.

LETTUCE PLANTS HAVING RESISTANCE TO *NASONOVIA RIBISNIGRI* BIOTYPE NR:1

CROSS-REFERENCE TO RELATED APPLICATIONS

This application claims the priority of U.S. Provisional Appl. Ser. No. 62/906,391, filed Sep. 26, 2019, which is incorporated herein by reference in its entirety.

INCORPORATION OF SEQUENCE LISTING

A sequence listing containing the file named "SEMB042US_ST25.txt" which is 41.2 kilobytes (measured in MS-Windows®) and created on Aug. 26, 2020, and comprises 95 sequences, is incorporated herein by reference in its entirety.

FIELD OF THE INVENTION

The present invention relates to methods and compositions for producing lettuce plants exhibiting increased resistance to the lettuce aphid *Nasonovia ribisnigri* biotype Nr:1.

BACKGROUND OF THE INVENTION

Host plant resistance is an important trait in agriculture, particularly in the area of food crop production. Although loci conferring resistance to pests have been identified in various lettuce species, efforts to introduce these loci into cultivated lines have been hindered by a lack of specific markers linked to the loci. The use of marker-assisted selection (MAS) in plant breeding has made it possible to select plants based on genetic markers linked to traits of interest. However, accurate markers for identifying or tracking desirable traits in plants are frequently unavailable even if a gene associated with the trait has been characterized. These difficulties are further complicated by factors such as polygenic or quantitative inheritance, epistasis, and an incomplete understanding of the genetic background underlying expression of a desired phenotype.

SUMMARY OF THE INVENTION

In one aspect, the present invention provides an elite *Lactuca sativa* plant comprising at least a first recombinant chromosomal segment from *Lactuca serriola* on chromosome 8, wherein said recombinant chromosomal segment comprises an allele conferring resistance to *Nasonovia ribisnigri* biotype Nr:1 relative to a plant lacking said recombinant chromosomal segment. In some embodiments, said first recombinant chromosomal segment comprises a marker locus selected from the group consisting of marker locus M1 (SEQ ID NO: 26), marker locus M2 (SEQ ID NO: 16), marker locus M4 (SEQ ID NO: 46), marker locus M5 (SEQ ID NO: 11), marker locus M7 (SEQ ID NO: 21), marker locus M8 (SEQ ID NO: 41), marker locus M10 (SEQ ID NO: 36), and marker locus M11 (SEQ ID NO: 31) on chromosome 8. In other embodiments, said *Nasonovia ribisnigri* biotype Nr:1 resistance allele is located between 106,984,777 bp and 136,545,853 bp on chromosome 8 of the public *Lactuca sativa* reference genome Lsat_Salinas_v7. In certain embodiments, the plant is homozygous for said recombinant chromosomal segment.

In addition, the present invention provides a plant part of an elite *Lactuca sativa* plant comprising at least a first recombinant chromosomal segment from *Lactuca serriola* on chromosome 8, wherein said recombinant chromosomal segment comprises an allele conferring resistance to *Nasonovia ribisnigri* biotype Nr:1 relative to a plant lacking said recombinant chromosomal segment. In certain embodiments, said plant part is a cell, a seed, a root, a stem, a leaf, a head, a flower, or pollen. In further embodiments, the invention provides a seed of an elite *Lactuca sativa* plant comprising at least a first recombinant chromosomal segment from *Lactuca serriola* on chromosome 8, wherein said recombinant chromosomal segment comprises an allele conferring resistance to *Nasonovia ribisnigri* biotype Nr:1 relative to a plant lacking said recombinant chromosomal segment.

The present invention also provides an elite *Lactuca sativa* plant comprising at least a first recombinant chromosomal segment from *Lactuca serriola* on chromosome 8, wherein said first recombinant chromosomal segment comprises an allele conferring resistance to *Nasonovia ribisnigri* biotype Nr:1 relative to a plant lacking said first recombinant chromosomal segment, and wherein said plant further comprises a second recombinant chromosomal segment on chromosome 4, wherein said second recombinant chromosomal segment comprises an allele conferring further improved resistance to *Nasonovia ribisnigri* biotype Nr:1 relative to a plant lacking said second recombinant chromosomal segment. In some embodiments, the second recombinant chromosomal segment comprises a marker selected from the group consisting of marker locus M13 (SEQ ID NO: 61), marker locus M14 (SEQ ID NO: 66), marker locus M15 (SEQ ID NO: 67), marker locus M16 (SEQ ID NO: 68), marker locus M17 (SEQ ID NO: 69), marker locus M18 (SEQ ID NO: 70), marker locus M19 (SEQ ID NO: 75), marker locus M20 (SEQ ID NO: 76), marker locus M21 (SEQ ID NO: 81), marker locus M22 (SEQ ID NO: 86), and marker locus M23 (SEQ ID NO: 91) on chromosome 4.

In addition, the present invention provides a plant part of an elite *Lactuca sativa* plant comprising at least a first recombinant chromosomal segment from *Lactuca serriola* on chromosome 8, wherein said first recombinant chromosomal segment comprises an allele conferring resistance to *Nasonovia ribisnigri* biotype Nr:1 relative to a plant lacking said first recombinant chromosomal segment, and wherein said plant further comprises a second recombinant chromosomal segment on chromosome 4, wherein said second recombinant chromosomal segment comprises an allele conferring further improved resistance to *Nasonovia ribisnigri* biotype Nr:1 relative to a plant lacking said second recombinant chromosomal segment, and wherein said plant part comprises said first and said second recombinant chromosomal segments. In certain embodiments, said plant part is a cell, a seed, a root, a stem, a leaf, a head, a flower, or pollen. In further embodiments, the invention provides a seed of an elite *Lactuca sativa* plant comprising at least a first recombinant chromosomal segment from *Lactuca serriola* on chromosome 8, wherein said first recombinant chromosomal segment comprises an allele conferring resistance to *Nasonovia ribisnigri* biotype Nr:1 relative to a plant lacking said first recombinant chromosomal segment, and wherein said plant further comprises a second recombinant chromosomal segment on chromosome 4, wherein said second recombinant chromosomal segment comprises an allele conferring further improved resistance to *Nasonovia ribisnigri* biotype Nr:1 relative to a plant lacking said second recombinant chromosomal segment. In yet further embodiments, a representative sample of seed of said plant comprising said first and said second recombinant chromosomal segments has been deposited under ATCC Accession No. PTA-126067.

In another aspect, the present invention provides a method for producing an elite *Lactuca sativa* plant with improved resistance to *Nasonovia ribisnigri* biotype Nr:1 comprising introgressing into said plant a *Nasonovia ribisnigri* biotype Nr:1 resistance allele within a recombinant chromosomal segment flanked in the genome of said plant by marker locus M5 (SEQ ID NO: 11) and marker locus M4 (SEQ ID NO: 46) on chromosome 8, wherein said introgressed *Nasonovia ribisnigri* biotype Nr:1 resistance allele confers to said plant resistance to *Nasonovia ribisnigri* biotype Nr:1 relative to a plant lacking said allele. In some embodiments, said introgressing comprises: a) crossing a plant comprising said recombinant chromosomal segment with itself or with a second *Lactuca sativa* plant of a different genotype to produce one or more progeny plants; and b) selecting a progeny plant comprising said recombinant chromosomal segment. In other embodiments, selecting a progeny plant comprises detecting nucleic acids comprising marker locus M1 (SEQ ID NO: 26), marker locus M2 (SEQ ID NO: 16), marker locus M4 (SEQ ID NO: 46), marker locus M5 (SEQ ID NO: 11), marker locus M7 (SEQ ID NO: 21), marker locus M8 (SEQ ID NO: 41), marker locus M10 (SEQ ID NO: 36), or marker locus M11 (SEQ ID NO: 31). In some embodiments, the progeny plant is an $F_2$-$F_6$ progeny plant. In other embodiments, said introgressing comprises backcrossing, marker-assisted selection or assaying for said resistance to *Nasonovia ribisnigri* biotype Nr:1. In further embodiments, said backcrossing comprises from 2-7 generations of backcrosses. In other embodiments, said plant further comprises a second introgressed *Nasonovia ribisnigri* biotype Nr:1 resistance allele within a recombinant chromosomal segment flanked in the genome of said plant by marker locus M5 (SEQ ID NO: 11) and marker locus M4 (SEQ ID NO: 46) on chromosome 8 or by marker locus M13 (SEQ ID NO: 61) and marker locus M23 (SEQ ID NO: 91) on chromosome 4. The present invention further provides *Lactuca sativa* plants obtainable by the methods provided herein.

The present invention also provides a method of selecting a *Lactuca sativa* plant exhibiting resistance to *Nasonovia ribisnigri* biotype Nr:1, comprising: a) crossing the *Lactuca sativa* plant of claim 1 with itself or with a second *Lactuca sativa* plant of a different genotype to produce one or more progeny plants; and b) selecting a progeny plant comprising said *Nasonovia ribisnigri* biotype Nr:1 resistance allele. In some embodiments, selecting said progeny plant detecting a marker locus genetically linked to said *Nasonovia ribisnigri* biotype Nr:1 resistance allele. In further embodiments, selecting said progeny plant comprises detecting a marker locus within or genetically linked to a chromosomal segment flanked in the genome of said plant by marker locus M5 (SEQ ID NO: 11) and marker locus M4 (SEQ ID NO: 46) on chromosome 8. In other embodiments, selecting a progeny comprises detecting nucleic acids comprising marker locus M1 (SEQ ID NO: 26), marker locus M2 (SEQ ID NO: 16), marker locus M4 (SEQ ID NO: 46), marker locus M5 (SEQ ID NO: 11), marker locus M7 (SEQ ID NO: 21), marker locus M8 (SEQ ID NO: 41), marker locus M10 (SEQ ID NO: 36), or marker locus M11 (SEQ ID NO: 31). In some embodiments, said progeny plant is an $F_2$-$F_6$ progeny plant. In other embodiments, producing said progeny plant comprises backcrossing.

DETAILED DESCRIPTION

Figure 1:
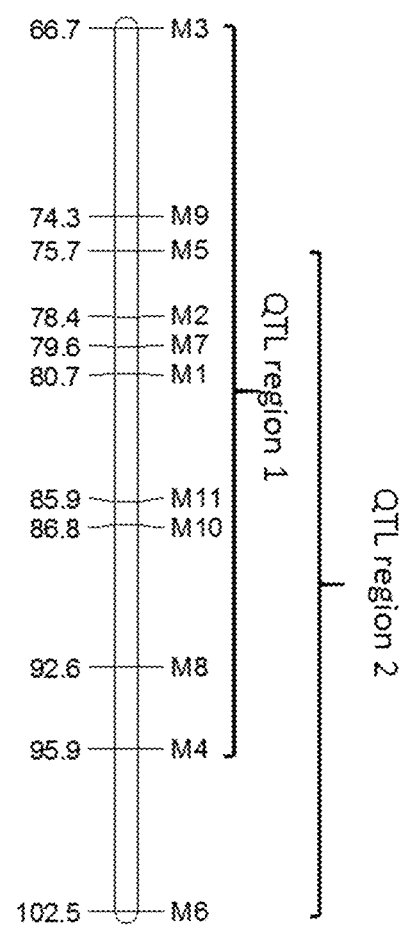
FIG. 1: Shows an overview of the genetic positions of the markers that are associated with the *Nasonovia ribisnigri* biotype Nr:1 resistance QTLs identified on chromosome 8.

*Lactuca sativa* L. (*L. sativa*) is a species belonging to the genus *Lactuca* and the family Asteraceae. This species is commercially referred to as lettuce. Lettuce is mostly grown as a leaf vegetable for fresh market consumption and is typically divided into seven main cultivar groups, each group having multiple varieties: (i) Leaf, loose-leaf, cutting or bunching lettuce; (ii) Romaine/Cos; (iii) Iceberg or Crisphead; (iv) Butterhead; (v) Summercrisp or Batavian; (vi) Celtuce or Stem; and (vii) Oilseed. Lettuce is closely related to several other *Lactuca* species including, but not limited to, the wild species *Lactuca serriola* (*L. serriola*). In contrast to *L. sativa*, *L. serriola* (also called prickly lettuce) is considered an aggressive weed of field crops that is found in temperate and subtropical zones.

Lettuce is a high-value crop that carries economic significance worldwide. In general, growers strive to produce lettuce that requires minimal processing and can be consumed directly. This requires lettuce heads to be free of insects at the time of harvest. Aphids are a major insect pest to lettuce crops, due to their short life cycle and ability to transmit plant viruses. *Nasonovia ribisnigri* (Mosley) (*N. ribisnigri*) is the major aphid species occurring in lettuce worldwide. The presence of aphids at harvest makes heads and salad packs unmarketable, resulting in significant financial losses for growers. As this species of aphids prefer to feed on the inner leaves of lettuce heads, the closed nature of the head in some lettuce types makes it difficult to apply pesticides that reach the feeding sites. Furthermore, there is an increasing consumer preference for pesticide-free crops. It is therefore necessary to identify and develop cultivars that have host plant resistance to *N. ribisnigri*.

The Nr gene from the wild lettuce species *Lactuca virosa* (*L. virosa*) was widely used as an effective mechanism for resistance against *N. ribisnigri* in cultivated lettuce varieties until about 2007. At that time, reports of populations of aphids able to infect lettuce varieties containing the Nr gene emerged in Europe, indicating a new resistance-breaking biotype of *N. ribisnigri*. While the Nr gene was effective against the previously characterized biotype (Nr:0), it was found to be ineffective against the new biotype. This new biotype was officially recognized as Nr:1 and has been responsible for lettuce crop losses all across Europe, including Spain, France, Germany, Netherlands, and the United Kingdom.

The invention represents a significant advance in the art by providing elite *L. sativa* plants having resistance to *N. ribisnigri* biotype Nr:1. Such plants can be referred to as plants of *N. ribisnigri* biotype Nr:1 resistant lettuce varieties. Methods of producing such *N. ribisnigri* biotype Nr:1 resistant lettuce plants, lines, and varieties are further provided. Also disclosed herein are molecular markers that are linked to quantitative trait loci (QTL) contributing to *N. ribisnigri* biotype Nr:1 resistance. Through use of such markers and the methods described herein, one of skill in the art may increase the degree of *N. ribisnigri* biotype Nr:1 resistance in lettuce plants and select plants for an increased predisposition for *N. ribisnigri* biotype Nr:1 resistance. In particular embodiments, the methods are performed on lettuce plants comprising one or more QTLs contributing to *N. ribisnigri* biotype Nr:1 resistance found in *L. serriola*.

*N. ribisnigri* biotype Nr:1 resistance sources have been identified in various *Lactuca* species. A study of *L. virosa* accessions, for example, identified *N. ribisnigri* biotype Nr:1 resistance QTLs on chromosomes 6 and 7 in the *L. virosa* accession PI273597 (WO 2016/066748). However, the resistance conferred by these QTLs was only evaluated in *L. virosa* plants and not in *L. sativa* plants. Furthermore, WO 2011/058192 reports a *L. serriola*-derived resistance to *N. ribisnigri* biotype Nr:1 as monogenic and dominant, while the same inventors report the *L. serriola*-derived resistance *N. ribisnigri* biotype Nr:1 as monogenic and recessive in WO 2012/066008 and WO 2012/065629. Furthermore, no genetic information, genetic/molecular markers, or resistance profile in an *L. sativa* background is provided for any disclosed *L. serriola*-derived resistance.

The present invention represents a significant advance in that it provides, in one embodiment, *N. ribisnigri* biotype Nr:1 resistance in lettuce plants conferred by a novel QTL on chromosome 8 as well as novel recombinant chromosomal segments from *L. serriola* comprising the QTL, as well as methods for the production thereof. In another embodiment, the present invention provides improved *N. ribisnigri* biotype Nr:1 resistance in lettuce plants conferred by a novel QTL on chromosome 4 when present with the novel QTL on chromosome 8, as well as novel recombinant chromosomal segments from *L. serriola* comprising the QTLs, including methods for the production thereof. It was surprisingly found that the QTLs could be deployed in combination to obtain an increased resistance. Novel markers for the new loci are provided herein, allowing the loci to be accurately introgressed and tracked during development of new varieties. As such, the invention permits introgression of the *N. ribisnigri* biotype Nr:1 resistance loci derived from *L. serriola* into potentially any desired elite lettuce variety.

In certain embodiments, plants are provided herein comprising an introgressed *N. ribisnigri* biotype Nr:1 resistance allele on chromosome 8, wherein said allele confers resistance to *N. ribisnigri* biotype Nr:1 relative to a plant not comprising the allele. In further embodiments, plants are provided comprising combinations of introgressed *N. ribisnigri* biotype Nr:1 resistance alleles on chromosomes 8 and 4.

In some embodiments, the introgressed *N. ribisnigri* biotype Nr:1 resistance allele is defined as located within a recombinant chromosomal segment from *L. serriola* flanked by marker locus M5 (SEQ ID NO: 11) and marker locus M4 (SEQ ID NO: 46) on chromosome 8. In other embodiments, such a segment can comprise one or more of marker locus M2 (SEQ ID NO: 16), marker locus M7 (SEQ ID NO: 21), marker locus M1 (SEQ ID NO: 26), marker locus M11 (SEQ ID NO: 31), marker locus M10 (SEQ ID NO: 36), and marker locus M8 (SEQ ID NO: 41). Marker locus M5 comprises a SNP change from T to C at 106,984,777 bp of the public *L. sativa* reference genome Lsat_Salinas_v7, marker locus M2 comprises a SNP change from A to T at 110,784,917 bp of the public *L. sativa* reference genome Lsat_Salinas_v7, marker locus M7 comprises a SNP change from C to T at 112,532,048 bp of the public *L. sativa* reference genome Lsat_Salinas_v7, marker locus M1 comprises a SNP change from T to C at 113,983,446 bp of the public *L. sativa* reference genome Lsat_Salinas_v7, marker locus M11 comprises a SNP change from C to T at 122,770,672 bp of the public *L. sativa* reference genome Lsat_Salinas_v7, marker locus M10 comprises a SNP change from T to C at 124,352,100 bp of the public *L. sativa* reference genome Lsat_Salinas_v7, marker locus M8 comprises a SNP change from C to G at 132,833,792 bp of the public *L. sativa* reference genome Lsat_Salinas_v7, and marker locus M4 comprises a SNP change from T to G at 136,545,853 bp of the public *L. sativa* reference genome Lsat_Salinas_v7. The public genome of lettuce is available at, for example lgr.genomecenter.ucdavis.edu, and one skilled in the art would understand how to locate the marker sequences provided for the first time in the instant application on any version (or later version) of the public genome.

Although *L. sativa* plants may contain the donor (*L. serriola*) allele at all indicated markers, the favorable allele for marker locus M5 (SEQ ID NO: 11) and marker locus M4 (SEQ ID NO: 46) flanking the QTL interval on chromosome 8 is the recurrent parent allele. For interstitial marker locus M2 (SEQ ID NO: 16), marker locus M7 (SEQ ID NO: 21), marker locus M1 (SEQ ID NO: 26), marker locus M11 (SEQ ID NO: 31), marker locus M10 (SEQ ID NO: 36), and marker locus M8 (SEQ ID NO: 41), the favorable allele is the allele from the donor parent.

In other embodiments, the invention provides plants comprising the novel recombinant chromosomal segment from *L. serriola* on chromosome 8 as well as a novel recombinant chromosomal segment from *L. serriola* on chromosome 4. Surprisingly, this combination provides additive resistance to *N. ribisnigri* biotype Nr: 1. Methods of producing such plants comprising the improved resistance are further provided. In some embodiments, the introgressed *N. ribisnigri* biotype Nr:1 resistance allele is defined as located on chromosome 4 within a recombinant chromosomal segment from *L. serriola* flanked by marker locus M13 (SEQ ID NO: 61) and marker locus M23 (SEQ ID NO: 91). In other embodiments, such a segment can comprise one or more of marker locus M14 (SEQ ID NO: 66), marker locus M15 (SEQ ID NO: 67), marker locus M16 (SEQ ID NO: 68), marker locus M17 (SEQ ID NO: 69), marker locus M18 (SEQ ID NO: 70), marker locus M19 (SEQ ID NO: 75), marker locus M20 (SEQ ID NO: 76), marker locus M21 (SEQ ID NO: 81), and marker locus M22 (SEQ ID NO: 86). Marker locus M13 comprises a SNP change from G to T at 309,028,468 bp of the public *L. sativa* reference genome Lsat_Salinas_v7, marker locus M14 comprises a SNP change from C to T at 317,543,051 bp of the public *L. sativa* reference genome Lsat_Salinas_v7, marker locus M15 comprises a SNP change from C to T at 324,002,441 bp of the public *L. sativa* reference genome Lsat_Salinas_v7, marker locus M16 comprises a SNP change from A to T at 331,652,666 bp of the public *L. sativa* reference genome Lsat_Salinas_v7, marker locus M17 comprises a SNP change from C to T at 341,160,568 bp of the public *L. sativa* reference genome Lsat_Salinas_v7, marker locus M18 comprises a SNP change from A to G at 348,314,352 bp of the public *L. sativa* reference genome Lsat_Salinas_v7, marker locus M19 comprises a SNP change from A to T at 357,158,000 bp of the public *L. sativa* reference genome Lsat_Salinas_v7; marker locus M20 comprises a SNP change from C to T at 361,400,802 bp of the public *L. sativa* reference genome Lsat_Salinas_v7, marker locus M21 comprises a SNP change from C to T at 365,781,913 bp of the public *L. sativa* reference genome Lsat_Salinas_v7, marker locus M22 comprises a SNP change from C to T at 371,266,283 bp of the public *L. sativa* reference genome Lsat_Salinas_v7, and marker locus M23 comprises a SNP change from C to T at 373,021,175 bp of the public *L. sativa* reference genome Lsat_Salinas_v7. The public genome of lettuce is available at, for example lgr.genomecenter.ucdavis.edu, and one skilled in the art would understand how to locate the marker sequences provided for the first time in the instant application on any version (or later version) of the public genome.

Table 2 also indicates the nucleotide of the donor (*L. serriola*) allele present at the SNP position (the nucleotide of the recurrent parent allele is thus the alternative indicated for the SNP position). Although *L. sativa* plants may contain the donor allele at all indicated markers, the favorable alleles for marker locus M13 (SEQ ID NO: 61) and marker locus M23 (SEQ ID NO: 91) flanking the QTL interval on chromosome 4 are preferably the recurrent parent alleles. For interstitial marker locus M14 (SEQ ID NO: 66), marker locus M15 (SEQ ID NO: 67), marker locus M16 (SEQ ID NO: 68), marker locus M17 (SEQ ID NO: 69), marker locus M18 (SEQ ID NO: 70), marker locus M19 (SEQ ID NO: 75), marker locus M20 (SEQ ID NO: 76), marker locus M21 (SEQ ID NO: 81), and marker locus M22 (SEQ ID NO: 86), the favorable allele is the allele from the donor parent.

In certain embodiments, the invention provides methods of producing or selecting a lettuce plant exhibiting resistance to *N. ribisnigri* Nr:1 comprising: a) crossing a lettuce plant provided herein with itself or with a second lettuce plant of a different genotype to produce one or more progeny plants; and b) selecting a progeny plant comprising a *N. ribisnigri* biotype Nr:1 resistance allele. In some embodiments, methods of the invention comprise selecting a progeny plant by detecting nucleic acids comprising marker locus M1 (SEQ ID NO: 26), marker locus M2 (SEQ ID NO: 16), marker locus M4 (SEQ ID NO: 46), marker locus M5 (SEQ ID NO: 11), marker locus M7 (SEQ ID NO: 21), marker locus M8 (SEQ ID NO: 41), marker locus M10 (SEQ ID NO: 36), or marker locus M11 (SEQ ID NO: 31).

Because genetically diverse plant lines can be difficult to cross, the introgression of *N. ribisnigri* biotype Nr:1 resistance loci and/or alleles into cultivated lines using conventional breeding methods could require prohibitively large segregating populations for progeny screens with an uncertain outcome. Marker-assisted selection (MAS) is therefore essential for the effective introgression of loci that confer resistance to *N. ribisnigri* biotype Nr:1 into elite cultivars. For the first time, the present invention enables effective MAS by providing improved and validated markers for detecting genotypes associated with *N. ribisnigri* biotype Nr:1 resistance without the need to grow large populations of plants to maturity in order to observe the phenotype.

I. Genomic Regions, Loci, and Polymorphisms in Lettuce Associated With Resistance to *Nasonovia ribisnigri* Biotype Nr:1

The invention provides novel introgressions of one or more loci associated with resistance to *N. ribisnigri* biotype Nr:1 in lettuce, together with polymorphic nucleic acids and linked markers for tracking the introgressions during plant breeding.

The inventors have identified more than 20 *L. serriola* accessions resistant to *N. ribisnigri* biotype Nr:1. Any of the known *L. serriola* accessions can be screened for resistance and used as a source for the introgression fragments described herein. As *L. serriola* is a wild species, accessions can also be collected from regions in which it was originally found, such as in Europe, Asia, and north Africa. In addition, accessions of *L. serriola* are available from genebanks including Centre for Genetic Resources, the Netherlands (CGN), Wageningen, the Netherlands and the National Plant Germplasm System of the US Department of Agriculture (USDA). In addition, the seeds deposited under ATCC Accession No. PTA-126067 may be used as a source for the recombinant chromosomal segment on chromosome 8, as well as the recombinant introgression on chromosome 4.

In one embodiment, the invention provides materials and methods for obtaining a locus conferring resistance to *N. ribisnigri* biotype Nr:1 from any additional accessions of *L. serriola*. Using the information set forth herein, including, but not limited to the polymorphic markers provided herein, the resistance to *N. ribisnigri* biotype Nr:1 from *L. serriola* can be introgressed into *L. sativa* varieties without the poor agronomic properties otherwise associated with *L. serriola*.

Using the improved genetic markers and assays of the invention, the present inventors were able to successfully identify novel introgressions that confer to a lettuce plant resistance to *N. ribisnigri* biotype Nr:1. In certain embodiments, the invention provides lettuce plants comprising donor DNA between marker locus M5 (SEQ ID NO: 11) and marker locus M4 (SEQ ID NO: 46) on chromosome 8, and/or marker locus M13 (SEQ ID NO: 61) and marker locus M23 (SEQ ID NO: 91) on chromosome 4.

II. Introgression of Genomic Regions Associated With Resistance to *Nasonovia ribisnigri* Biotype Nr:1

Marker-assisted introgression involves the transfer of a chromosomal region defined by one or more markers from a first genetic background to a second. Offspring of a cross that contain the introgressed genomic region can be identified by the combination of markers characteristic of the desired introgressed genomic region from a first genetic background and both linked and unlinked markers characteristic of the second genetic background.

The present invention provides novel accurate markers for identifying and tracking introgression of one or more of the genomic regions disclosed herein from a *N. ribisnigri* biotype Nr:1 resistant plant into a cultivated line. The invention further provides markers for identifying and tracking the novel introgressions disclosed herein during plant breeding, including the markers set forth in Tables 1 and 2.

Markers within or linked to any of the genomic intervals of the present invention may be useful in a variety of breeding efforts that include introgression of genomic regions associated with pest resistance into a desired genetic background. For example, a marker within 40 cM, 20 cM, 15 cM, 10 cM, 5 cM, 2 cM, or 1 cM of a marker associated with pest resistance described herein can be used for marker-assisted introgression of genomic regions associated with a pest resistant phenotype.

Lettuce plants comprising one or more introgressed regions associated with a desired phenotype wherein at least 10%, 25%, 50%, 75%, 90%, or 99% of the remaining genomic sequences carry markers characteristic of the recurrent parent germplasm are also provided. Lettuce plants comprising an introgressed region comprising regions closely linked to or adjacent to the genomic regions and markers provided herein and associated with a pest resistance phenotype are also provided.

III. Development of Lettuce Varieties Resistant to *Nasonovia ribisnigri* Biotype Nr:1

For most breeding objectives, commercial breeders work with germplasm that is "cultivated," "cultivated type," or "elite." This germplasm is easier to breed because it generally performs well when evaluated for horticultural performance. A number of cultivated lettuce types have been developed, including L. sativa, which is agronomically elite and appropriate for commercial cultivation. Lettuce cultivar groups include, but are not limited to, the Cos, Cutting, Stalk (or Asparagus), Butterhead, Crisphead (or Iceberg or Cabbage), Latin and Oilseed groups (De Vries, *Gen. Resources and Crop Evol.* 44:165-174, 1997). However, the performance advantage a cultivated germplasm provides can be offset by a lack of allelic diversity. Breeders generally accept this tradeoff because progress is faster when working with cultivated material than when breeding with genetically diverse sources.

In contrast, when cultivated germplasm is crossed with non-cultivated germplasm, a breeder can gain access to novel alleles from the non-cultivated type. However, this approach presents significant difficulties due to fertility problems associated with crosses between diverse lines, and negative linkage drag from the non-cultivated parent. In lettuce plants, non-cultivated types such as *L. serriola* can provide alleles associated with disease resistance. However, these non-cultivated types may have poor horticultural qualities.

The process of introgres sing desirable resistance genes from non-cultivated lines into elite cultivated lines while avoiding problems with genetically linked deleterious loci or low heritability is a long and often arduous process. In deploying loci derived from wild relatives it is often desirable to introduce a minimal or truncated introgression that provides the desired trait but lacks detrimental effects. To aid introgression reliable marker assays are preferable to phenotypic screens. Success is furthered by simplifying genetics for key attributes to allow focus on genetic gain for quantitative traits such as pest resistance. Moreover, the process of introgressing genomic regions from non-cultivated lines can be greatly facilitated by the availability of accurate markers for MAS.

One of skill in the art would therefore understand that the loci, polymorphisms, and markers provided by the invention allow the tracking and introduction of any of the genomic regions identified herein into any genetic background. In addition, the genomic regions associated with pest resistance disclosed herein can be introgressed from one genotype to another and tracked using MAS. Thus, the inventors' discovery of accurate markers associated with pest resistance will facilitate the development of lettuce plants having beneficial phenotypes. For example, seed can be genotyped using the markers of the present invention to select for plants comprising desired genomic regions associated with pest resistance. Moreover, MAS allows identification of plants homozygous or heterozygous for a desired introgression.

Inter-species crosses can also result in suppressed recombination and plants with low fertility or fecundity. For example, suppressed recombination has been observed for the tomato nematode resistance gene Mi, the Mla and Mlg genes in barley, the Yr17 and Lr20 genes in wheat, the Run1 gene in grapevine, and the Rma gene in peanut. Meiotic recombination is essential for classical breeding because it enables the transfer of favorable loci across genetic backgrounds, the removal of deleterious genomic fragments, and pyramiding traits that are genetically tightly linked. Therefore, suppressed recombination forces breeders to enlarge segregating populations for progeny screens in order to arrive at the desired genetic combination.

Phenotypic evaluation of large populations is time-consuming, resource-intensive and not reproducible in every environment. Marker-assisted selection offers a feasible alternative. Molecular assays designed to detect unique polymorphisms, such as SNPs, are versatile. However, they may fail to discriminate loci within and among lettuce species in a single assay. Structural rearrangements of chromosomes such as deletions impair hybridization and extension of synthetically labeled oligonucleotides. In the case of duplication events, multiple copies are amplified in a single reaction without distinction. The development and validation of accurate and highly predictive markers are therefore essential for successful MAS breeding programs.

IV. Marker Assisted Breeding and Genetic Engineering Techniques

Genetic markers that can be used in the practice of the present invention include, but are not limited to, restriction fragment length polymorphisms (RFLPs), amplified fragment length polymorphisms (AFLPs), simple sequence repeats (SSRs), simple sequence length polymorphisms (SSLPs), single nucleotide polymorphisms (SNPs), insertion/deletion polymorphisms (Indels), variable number tandem repeats (VNTRs), and random amplified polymorphic DNA (RAPD), isozymes, and other markers known to those skilled in the art. Marker discovery and development in crop plants provides the initial framework for applications to marker-assisted breeding activities (U.S. Patent Pub. Nos. 2005/0204780, 2005/0216545, 2005/0218305, and 2006/00504538). The resulting "genetic map" is the representation of the relative position of characterized loci (polymorphic nucleic acid markers or any other locus for which loci can be identified) to each other.

Polymorphisms comprising as little as a single nucleotide change can be assayed in a number of ways. For example, detection can be made by electrophoretic techniques including a single strand conformational polymorphism (Orita et al. (1989) *Genomics,* 8(2), 271-278), denaturing gradient gel electrophoresis (Myers (1985) EP 0273085), or cleavage fragment length polymorphisms (Life Technologies, Inc., Gaithersburg, Md.), but the widespread availability of DNA sequencing often makes it easier to simply sequence amplified products directly. Once the polymorphic sequence difference is known, rapid assays can be designed for progeny testing, typically involving some version of PCR amplification of specific loci (PASA; Sommer et al. (1992) *Biotechniques* 12(1), 82-87), or PCR amplification of multiple specific loci (PAMSA; Dutton and Sommer (1991) *Biotechniques,* 11(6), 700-7002).

Polymorphic markers serve as useful tools for assaying plants for determining the degree of identity of lines or varieties (U.S. Pat. No. 6,207,367). These markers form the basis for determining associations with phenotypes and can be used to drive genetic gain. In certain embodiments of methods of the invention, polymorphic nucleic acids can be used to detect in a lettuce plant a genotype associated with pest resistance, identify a lettuce plant with a genotype associated with pest resistance, and to select a lettuce plant with a genotype associated with pest resistance. In certain embodiments of methods of the invention, polymorphic nucleic acids can be used to produce a lettuce plant that comprises in its genome an introgressed locus associated with pest resistance. In certain embodiments of the invention, polymorphic nucleic acids can be used to breed progeny lettuce plants comprising a locus or loci associated with pest resistance.

Genetic markers may include "dominant" or "codominant" markers. "Codominant" markers reveal the presence of two or more loci (two per diploid individual). "Dominant" markers reveal the presence of only a single locus. Markers are preferably inherited in codominant fashion so that the presence of both loci at a diploid locus, or multiple loci in triploid or tetraploid loci, are readily detectable, and they are free of environmental variation, i.e., their heritability is 1. A marker genotype typically comprises two marker loci at each locus in a diploid organism. The marker allelic composition of each locus can be either homozygous or heterozygous. Homozygosity is a condition where both loci at a locus are characterized by the same nucleotide sequence. Heterozygosity refers to a condition where the two loci at a locus are different.

Nucleic acid-based analyses for determining the presence or absence of the genetic polymorphism (i.e. for genotyping) can be used in breeding programs for identification, selection, introgression, and the like. A wide variety of genetic markers for the analysis of genetic polymorphisms are available and known to those of skill in the art. The analysis may be used to select for genes, portions of genes, QTL, loci, or genomic regions that comprise or are linked to a genetic marker that is linked to or associated with pest resistance in lettuce plants.

As used herein, nucleic acid analysis methods include, but are not limited to, PCR-based detection methods (for example, TaqMan assays), microarray methods, mass spectrometry-based methods and/or nucleic acid sequencing methods, including whole genome sequencing. In certain embodiments, the detection of polymorphic sites in a sample of DNA, RNA, or cDNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means.

One method of achieving such amplification employs the polymerase chain reaction (PCR) (Mullis et al. (1986) Cold Spring Harbor Symp. *Quant. Biol.* 51:263-273; European Patent 50,424; European Patent 84,796; European Patent 258,017; European Patent 237,362; European Patent 201,184; U.S. Pat. Nos. 4,683,202; 4,582,788; and 4,683,194), using primer pairs that are capable of hybridizing to the proximal sequences that define a polymorphism in its double-stranded form. Methods for typing DNA based on mass spectrometry can also be used. Such methods are disclosed in U.S. Pat. Nos. 6,613,509 and 6,503,710, and references found therein.

Polymorphisms in DNA sequences can be detected or typed by a variety of effective methods well known in the art including, but not limited to, those disclosed in U.S. Pat. Nos. 5,468,613, 5,217,863; 5,210,015; 5,876,930; 6,030,787; 6,004,744; 6,013,431; 5,595,890; 5,762,876; 5,945,283; 5,468,613; 6,090,558; 5,800,944; 5,616,464; 7,312,039; 7,238,476; 7,297,485; 7,282,355; 7,270,981 and 7,250,252 all of which are incorporated herein by reference in their entirety. However, the compositions and methods of the present invention can be used in conjunction with any polymorphism typing method to detect polymorphisms in genomic DNA samples. These genomic DNA samples used include but are not limited to, genomic DNA isolated directly from a plant, cloned genomic DNA, or amplified genomic DNA.

For instance, polymorphisms in DNA sequences can be detected by hybridization to locus-specific oligonucleotide (ASO) probes as disclosed in U.S. Pat. Nos. 5,468,613 and 5,217,863. U.S. Pat. No. 5,468,613 discloses locus specific oligonucleotide hybridizations where single or multiple nucleotide variations in nucleic acid sequence can be detected in nucleic acids by a process in which the sequence containing the nucleotide variation is amplified, spotted on a membrane and treated with a labeled sequence-specific oligonucleotide probe.

Target nucleic acid sequence can also be detected by probe ligation methods, for example as disclosed in U.S. Pat. No. 5,800,944 where sequence of interest is amplified and hybridized to probes followed by ligation to detect a labeled part of the probe.

Microarrays can also be used for polymorphism detection, wherein oligonucleotide probe sets are assembled in an overlapping fashion to represent a single sequence such that a difference in the target sequence at one point would result in partial probe hybridization (Borevitz et al., *Genome Res.* 13:513-523 (2003); Cui et al., *Bioinformatics* 21:3852-3858 (2005). On any one microarray, it is expected there will be a plurality of target sequences, which may represent genes and/or noncoding regions wherein each target sequence is represented by a series of overlapping oligonucleotides, rather than by a single probe. This platform provides for high throughput screening of a plurality of polymorphisms. Typing of target sequences by microarray-based methods is described in U.S. Pat. Nos. 6,799,122; 6,913,879; and 6,996,476.

Other methods for detecting SNPs and Indels include single base extension (SBE) methods. Examples of SBE methods include, but are not limited, to those disclosed in U.S. Pat. Nos. 6,004,744; 6,013,431; 5,595,890; 5,762,876; and 5,945,283.

In another method for detecting polymorphisms, SNPs and Indels can be detected by methods disclosed in U.S. Pat. Nos. 5,210,015; 5,876,930; and 6,030,787 in which an oligonucleotide probe having a 5' fluorescent reporter dye and a 3' quencher dye covalently linked to the 5' and 3' ends of the probe. When the probe is intact, the proximity of the reporter dye to the quencher dye results in the suppression of the reporter dye fluorescence, e.g. by Forster-type energy transfer. During PCR, forward and reverse primers hybridize to a specific sequence of the target DNA flanking a polymorphism while the hybridization probe hybridizes to polymorphism-containing sequence within the amplified PCR product. In the subsequent PCR cycle DNA polymerase with 5'→3' exonuclease activity cleaves the probe and separates the reporter dye from the quencher dye resulting in increased fluorescence of the reporter.

In another embodiment, a locus or loci of interest can be directly sequenced using nucleic acid sequencing technologies. Methods for nucleic acid sequencing are known in the art and include technologies provided by 454 Life Sciences (Branford, Conn.), Agencourt Bioscience (Beverly, Mass.), Applied Biosystems (Foster City, Calif.), LI-COR Biosciences (Lincoln, Nebr.), NimbleGen Systems (Madison, Wis.), Illumina (San Diego, Calif.), and VisiGen Biotechnologies (Houston, Tex.). Such nucleic acid sequencing technologies comprise formats such as parallel bead arrays, sequencing by ligation, capillary electrophoresis, electronic microchips, "biochips," microarrays, parallel microchips, and single-molecule arrays.

Various genetic engineering technologies have been developed and may be used by those of skill in the art to introduce traits in plants. In certain aspects of the claimed invention, traits are introduced into lettuce plants via altering or introducing a single genetic locus or transgene into the genome of a variety or progenitor thereof. Methods of genetic engineering to modify, delete, or insert genes and polynucleotides into the genomic DNA of plants are well-known in the art.

In specific embodiments of the invention, improved lettuce lines can be created through the site-specific modification of a plant genome. Methods of genetic engineering include, for example, utilizing sequence-specific nucleases such as zinc-finger nucleases (see, for example, U.S. Pat. Appl. Pub. No. 2011-0203012); engineered or native meganucleases; TALE-endonucleases (see, for example, U.S. Pat. Nos. 8,586,363 and 9,181,535); and RNA-guided endonucleases, such as those of the CRISPR/Cas systems (see, for example, U.S. Pat. Nos. 8,697,359 and 8,771,945 and U.S. Pat. Appl. Pub. No. 2014-0068797). One embodiment of the invention thus relates to utilizing a nuclease or any associated protein to carry out genome modification. This nuclease could be provided heterologously within donor template DNA for templated-genomic editing or in a separate molecule or vector. A recombinant DNA construct may also comprise a sequence encoding one or more guide RNAs to direct the nuclease to the site within the plant genome to be modified. Further methods for altering or introducing a single genetic locus include, for example, utilizing single-stranded oligonucleotides to introduce base pair modifications in a plant genome (see, for example Sauer et al., *Plant Physiol*, 170(4):1917-1928, 2016).

Methods for site-directed alteration or introduction of a single genetic locus are well-known in the art and include those that utilize sequence-specific nucleases, such as the aforementioned, or complexes of proteins and guide-RNA that cut genomic DNA to produce a double-strand break (DSB) or nick at a genetic locus. As is well-understood in the art, during the process of repairing the DSB or nick introduced by the nuclease enzyme, a donor template, transgene, or expression cassette polynucleotide may become integrated into the genome at the site of the DSB or nick. The presence of homology arms in the DNA to be integrated may promote the adoption and targeting of the insertion sequence into the plant genome during the repair process through homologous recombination or non-homologous end joining (NHEJ).

In another embodiment of the invention, genetic transformation may be used to insert a selected transgene into a plant of the invention or may, alternatively, be used for the preparation of transgenes which can be introduced by backcrossing. Methods for the transformation of plants that are well-known to those of skill in the art and applicable to many crop species include, but are not limited to, electroporation, microprojectile bombardment, *Agrobacterium*-mediated transformation, and direct DNA uptake by protoplasts.

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

An efficient method for delivering transforming DNA segments to plant cells is microprojectile bombardment. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target cells. The screen disperses the particles so that they are not delivered to the recipient cells in large aggregates. Microprojectile bombardment techniques are widely applicable and may be used to transform virtually any plant species.

*Agrobacterium*-mediated transfer is another widely applicable system for introducing gene loci into plant cells. An advantage of the technique is that DNA can be introduced into whole plant tissues, thereby bypassing the need for regeneration of an intact plant from a protoplast. Modern *Agrobacterium* transformation vectors are capable of replication in *E. coli* as well as *Agrobacterium*, allowing for convenient manipulations (Klee et al., *Nat. Biotechnol.*, 3(7):637-642, 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes. Additionally, *Agrobacterium* containing both armed and disarmed Ti genes can be used for transformation.

In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells is well known in the art (Fraley et al., *Nat. Biotechnol.*, 3:629-635, 1985; U.S. Pat. No. 5,563,055).

Transformation of plant protoplasts also can be achieved using methods based on calcium phosphate precipitation, polyethylene glycol treatment, electroporation, and combinations of these treatments (see, for example, Potrykus et al., *Mol. Gen. Genet.*, 199:183-188, 1985; Omirulleh et al., *Plant Mol. Biol.*, 21(3):415-428, 1993; Fromm et al., *Nature*, 312:791-793, 1986; Uchimiya et al., *Mol. Gen. Genet.*, 204:204, 1986; Marcotte et al., *Nature*, 335:454, 1988). Transformation of plants and expression of foreign genetic elements is exemplified in Choi et al. (*Plant Cell Rep.*, 13:344-348, 1994), and Ellul et al. (*Theor. Appl. Genet.*, 107:462-469, 2003).

V. Definitions

The following definitions are provided to better define the present invention and to guide those of ordinary skill in the art in the practice of the present invention. Unless otherwise noted, terms are to be understood according to conventional usage by those of ordinary skill in the relevant art.

As used herein, the term "plant" includes plant cells, plant protoplasts, plant cells of tissue culture from which lettuce plants can be regenerated, plant calli, plant clumps and plant cells that are intact in plants or parts of plants such as pollen, flowers, seeds, leaves, stems, and the like.

As used herein, the term "population" means a genetically heterogeneous collection of plants that share a common parental derivation.

As used herein, the terms "variety" and "cultivar" mean a group of similar plants that by their genetic pedigrees and performance can be identified from other varieties within the same species.

As used herein, an "allele" refers to one of two or more alternative forms of a genomic sequence at a given locus on a chromosome.

A "quantitative trait locus" (QTL) is a chromosomal location that encodes for at least a first locus that affects the expressivity of a phenotype.

As used herein, a "marker" means a detectable characteristic that can be used to discriminate between organisms. Examples of such characteristics include, but are not limited to, genetic markers, biochemical markers, metabolites, morphological characteristics, and agronomic characteristics.

As used herein, the term "phenotype" means the detectable characteristics of a cell or organism that can be influenced by gene expression.

As used herein, the term "genotype" means the specific allelic makeup of a plant.

As used herein, "elite" or "cultivated" variety means any variety that has resulted from breeding and selection for superior agronomic performance. An "elite plant" refers to a plant belonging to an elite variety. Numerous elite varieties are available and known to those of skill in the art of lettuce breeding. An "elite population" is an assortment of elite individuals or varieties that can be used to represent the state of the art in terms of agronomically superior genotypes of a given crop species, such as lettuce. Similarly, an "elite germplasm" or elite strain of germplasm is an agronomically superior germplasm.

As used herein, the term "introgressed," when used in reference to a genetic locus, refers to a genetic locus that has been introduced into a new genetic background, such as through backcrossing. Introgression of a genetic locus can be achieved through plant breeding methods and/or by molecular genetic methods. Such molecular genetic methods include, but are not limited to, various plant transformation techniques and/or methods that provide for homologous recombination, non-homologous recombination, site-specific recombination, and/or genomic modifications that provide for locus substitution or locus conversion.

As used herein, the terms "recombinant" or "recombined" in the context of a chromosomal segment refer to recombinant DNA sequences comprising one or more genetic loci in a configuration in which they are not found in nature, for example as a result of a recombination event between homologous chromosomes during meiosis.

As used herein, the term "linked," when used in the context of nucleic acid markers and/or genomic regions, means that the markers and/or genomic regions are located on the same linkage group or chromosome such that they tend to segregate together at meiosis.

As used herein, "tolerance locus" means a locus associated with tolerance or resistance to disease or pest. For instance, a tolerance locus according to the present invention may, in one embodiment, control tolerance or susceptibility to N. ribisnigri biotype Nr:1.

As used herein, "tolerance" or "improved tolerance" in a plant refers to the ability of the plant to perform well, for example by maintaining yield, under disease conditions or upon pest infestations. Tolerance may also refer to the ability of a plant to maintain a plant vigor phenotype under disease conditions or under pest infestations. Tolerance is a relative term, indicating that a "tolerant" plant is more able to maintain performance compared to a different (less tolerant) plant (e.g. a different plant variety) grown in similar disease conditions or under similar pest pressure. One of skill will appreciate that plant tolerance to disease or pest conditions varies widely and can represent a spectrum of more-tolerant or less-tolerant phenotypes. However, by simple observation, one of skill can generally determine the relative tolerance of different plants, plant varieties, or plant families under disease or pest conditions, and furthermore, will also recognize the phenotypic gradations of "tolerance."

As used herein "resistance" or "improved resistance" in a plant to disease or pest conditions is an indication that the plant is more able to reduce disease or pest burden than a non-resistant or less resistant plant. Resistance is a relative term, indicating that a "resistant" plant is more able to reduce disease burden or pest burden compared to a different (less resistant) plant (e.g., a different plant variety) grown in similar disease conditions or pest pressure. One of skill will appreciate that plant resistance to disease conditions or pest infestation varies widely and can represent a spectrum of more-resistant or less-resistant phenotypes. However, by simple observation, one of skill can generally determine the relative resistance of different plants, plant varieties, or plant families under disease conditions or pest pressure, and furthermore, will also recognize the phenotypic gradations of "resistant."

As used herein, "resistance allele" means the nucleic acid sequence associated with tolerance or resistance to pest infestation.

"Sequence identity" and "sequence similarity" can be determined by alignment of r two nucleotide sequences using global or local alignment algorithms. Sequences may then be referred to as "substantially identical" or "essentially similar" when they are optimally aligned by for example the programs GAP or BESTFIT or the Emboss program "Needle" (using default parameters) share at least a certain minimal percentage of sequence identity. These programs use the Needleman and Wunsch global alignment algorithm to align two sequences over their entire length, maximizing the number of matches and minimizing the number of gaps. Generally, the default parameters are used, with a gap creation penalty=10 and gap extension penalty=0.5 (both for nucleotide and protein alignments). For nucleotides the default scoring matrix used is DNAFULL (Henikoff & Henikoff, PNAS 89:10915-10919; 1992). Sequence alignments and scores for percentage sequence identity may for example be determined using computer programs, such as EMBOSS as available on the world wide web under ebi.ac.uk/Tools/psa/emboss_needle/. Alternatively, sequence similarity or identity may be determined by searching against databases such as FASTA, BLAST, etc., but hits should be retrieved and aligned pairwise to compare sequence identity. Two nucleic acid sequences have "substantial sequence identity" if the percentage sequence identity is at least 85%, 90%, 95%, 98%, 99% or more (e.g. at least 99.1, 99.2 99.3 99.4, 99.5, 99.6, 99.7, 99.8, 99.9 (as determined by Emboss "needle" using default parameters, i.e. gap creation penalty=10, gap extension penalty=0.5, using scoring matrix DNAFULL for nucleic acids)). Markers may sometimes exhibit variation, particularly in regions which are not recognized by the probes.

The term "about" is used to indicate that a value includes the standard deviation of error for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and to "and/or." When used in conjunction with the word "comprising" or other open language in the claims, the words "a" and "an" denote "one or more," unless specifically noted. The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits.

VI. Deposit Information

A deposit was made of at least 625 seeds of lettuce line JA_BAG-JA19-0689, which comprises the introgressions from *Lactuca serriola*, as described herein. The deposit was made with the American Type Culture Collection (ATCC), 10801 University Boulevard, Manassas, Va. 20110-2209 USA. The deposit is assigned ATCC Accession No. PTA-126067, and the date of deposit was Jul. 24, 2019. Access to the deposit will be available during the pendency of the application to persons entitled thereto upon request. The deposit has been accepted under the Budapest Treaty and will be maintained in the ATCC Depository, which is a public depository, for a period of 30 years, or 5 years after the most recent request, or for the enforceable life of the patent, whichever is longer, and will be replaced if nonviable during that period. Applicant does not waive any infringement of their rights granted under this patent or any other form of variety protection, including the Plant Variety Protection Act (7 U.S.C. 2321 et seq.).

EXAMPLES

Example 1

Mapping of *Nasonovia ribisnigri* Biotype Nr:1 Resistance in Lettuce

More than 20 accessions resistant to *N. ribisnigri* biotype Nr:1 were identified during a large-scale screen of *L. serriola* lines. A subset of these accessions were crossed with a susceptible elite *L. sativa* line to create mapping populations. $F_2$ populations derived from these crosses were tested for resistance to *N. ribisnigri* biotype Nr:1 using a variation of the non-choice resistance assay. A randomized complete block design with 3 blocks and 4 replications (a total of 12 plants/family) was used. Parental lines and pathology controls were included in each replication with a total of 16 plants/control. Seeds were first sown in rock wool flats and after 4 weeks were transplanted into 8.5 cm pots with soil. At 6 weeks, the plants were each inoculated with 4 similarly-sized aphids of biotype Nr:1 and covered with a perforated bag to keep the aphids confined to the plants they were placed on. The trial was scored by counting the number of aphids on the plant 14 days post inoculation. In addition, tissue was taken from the plants used in these assays for genotyping at more than 2000 marker loci. Of this initial marker set, more than 900 markers were selected to map the genetic region conferring resistance to *N. ribisnigri* biotype Nr:1. The initial mapping revealed a region on chromosome 8 that explained approximately 28% of the phenotypic variation in resistance to *N. ribisnigri* biotype Nr:1. Marker M1 (SEQ ID NO: 26) was identified as the marker closest to the peak of the QTL.

In further mapping experiments, several different *L. serriola* accessions were crossed to an elite *L. sativa* line of the Butterhead variety and two overlapping genomic regions on chromosome 8 were found. For one set of accessions, a 29 cM region between markers M3 (SEQ ID NO: 1) and M4 (SEQ ID NO: 46) was identified, whereas for another set of accessions, a 27 cM region between markers M5 (SEQ ID NO: 11) and M6 (SEQ ID NO: 51) was identified. These regions overlap between markers M4 (SEQ ID NO: 46) and M5 (SEQ ID NO: 11). Marker M1 (SEQ ID NO: 26) lies within the genomic region between markers M4 (SEQ ID NO: 46) and M5 (SEQ ID NO: 11), therefore confirming the QTL peak identified in the initial mapping experiment. The genomic region conferring *N. ribisnigri* biotype Nr:1 resistance is therefore located between markers M4 (SEQ ID NO: 46) and M5 (SEQ ID NO: 11) on chromosome 8. Additional markers M2 (SEQ ID NO: 16), M7 (SEQ ID NO: 21), M8 (SEQ ID NO: 41), M9 (SEQ ID NO: 6), M10 (SEQ ID NO: 36), and M11 (SEQ ID NO: 31) were identified within the region flanked by markers M4 (SEQ ID NO: 46) and M5 (SEQ ID NO: 11). Table 1 shows the markers associated with the *N. ribisnigri* biotype Nr:1 resistance QTL on chromosome 8 that can be used for tracking and selection of the locus.

TABLE 1

Markers to track *L. serriola*-derived resistance to *N. ribisnigri* biotype Nr:1 on chromosome 8.

| Marker | Chr | Favorable Allele | SNP change | SNP position in marker (bp) | Position (cM) | SNP Position in Public Genome (bp) | Marker Sequence (SEQ ID NO) | Fwd Primer (SEQ ID NO) | Rev Primer (SEQ ID NO) | Probe 1 (SEQ ID NO) | Probe 2 (SEQ ID NO) |
|---|---|---|---|---|---|---|---|---|---|---|---|
| M3 | 8 | C | C/G | 61 | 66.69 | 94,407,370 | 1 | 2 | 3 | 4 | 5 |
| M9 | 8 | A | A/G | 430 | 74.30 | 105,094,422 | 6 | 7 | 8 | 9 | 10 |
| M5 | 8 | C | T/C | 61 | 75.68 | 106,984,777 | 11 | 12 | 13 | 14 | 15 |
| M2 | 8 | A | A/T | 61 | 78.39 | 110,784,917 | 16 | 17 | 18 | 19 | 20 |
| M7 | 8 | T | C/T | 196 | 79.63 | 112,532,048 | 21 | 22 | 23 | 24 | 25 |
| M1 | 8 | C | T/C | 61 | 80.67 | 113,983,446 | 26 | 27 | 28 | 29 | 30 |
| M11 | 8 | C | C/T | 101 | 85.85 | 122,770,672 | 31 | 32 | 33 | 34 | 35 |
| M10 | 8 | T | T/C | 101 | 86.76 | 124,352,100 | 36 | 37 | 38 | 39 | 40 |
| M8 | 8 | C | C/G | 61 | 92.64 | 132,833,792 | 41 | 42 | 43 | 44 | 45 |
| M4 | 8 | G | T/G | 101 | 95.93 | 136,545,853 | 46 | 47 | 48 | 49 | 50 |
| M6 | 8 | A | A/C | 101 | 102.46 | 143,313,652 | 51 | 52 | 53 | 54 | 55 |

In addition to the QTL on chromosome 8, a QTL on chromosome 4 was identified. The QTL was originally mapped to a region on the chromosome located between markers M12 (SEQ ID NO: 56) and M23 (SEQ ID NO: 91). To fine map the locus on chromosome 4, markers M13 (SEQ ID NO: 61), M14 (SEQ ID NO: 66), M15 (SEQ ID NO: 67), M16 (SEQ ID NO: 68), M17 (SEQ ID NO: 69), M18 (SEQ ID NO: 70), M19 (SEQ ID NO: 75), M20 (SEQ ID NO: 76), M21 (SEQ ID NO: 81), and M22 (SEQ ID NO: 86) were developed. The QTL was further fine mapped as being located between markers M13 (SEQ ID NO: 61) and M22 (SEQ ID NO: 86). Table 2 shows markers associated with the *N. ribisnigri* biotype Nr:1 resistance QTL on chromosome 4 that can be used for tracking and selection of the locus.

TABLE 2

Markers to track *L. serriola*-derived resistance to *N. ribisnigri* biotype Nr:1 on chromosome 4.

| Marker | Chr | Favorable Allele | SNP change | SNP position in marker (bp) | Position (cM) | SNP Position in Public Genome (bp) | Marker Sequence (SEQ ID NO) | Fwd Primer (SEQ ID NO) | Rev Primer (SEQ ID NO) | Probe 1 (SEQ ID NO) | Probe 2 (SEQ ID NO) |
|---|---|---|---|---|---|---|---|---|---|---|---|
| M12 | 4 | T | G/T | 81 | 183.03 | 296,011,799 | 56 | 57 | 58 | 59 | 60 |
| M13 | 4 | G | G/T | 343 | 188.20 | 309,028,468 | 61 | 62 | 63 | 64 | 65 |
| M14 | 4 | C | C/T | 101 | 192.44 | 317,543,051 | 66 | n/a | n/a | n/a | n/a |
| M15 | 4 | C | C/T | 101 | 195.95 | 324,002,441 | 67 | n/a | n/a | n/a | n/a |
| M16 | 4 | T | A/T | 101 | 200.29 | 331,652,666 | 68 | n/a | n/a | n/a | n/a |
| M17 | 4 | C | C/T | 61 | 206.32 | 341,160,568 | 69 | n/a | n/a | n/a | n/a |
| M18 | 4 | A | A/G | 61 | 211.00 | 348,314,352 | 70 | 71 | 72 | 73 | 74 |
| M19 | 4 | A | A/T | 101 | 216.50 | 357,158,000 | 75 | n/a | n/a | n/a | n/a |
| M20 | 4 | C | C/T | 61 | 219.08 | 361,400,802 | 76 | 77 | 78 | 79 | 80 |
| M21 | 4 | C | C/T | 61 | 221.73 | 365,781,913 | 81 | 82 | 83 | 84 | 85 |
| M22 | 4 | C | C/T | 537 | 225.00 | 371,266,283 | 86 | 87 | 88 | 89 | 90 |
| M23 | 4 | C | C/T | 443 | 226.00 | 373,021,175 | 91 | 92 | 93 | 94 | 95 |

Furthermore, it was determined for all phenotypically resistant plants that the QTL region on chromosome 8 and chromosome 4 has a *L. serriola* origin, whereas the genomic region in the QTL region on chromosome 8 and chromosome 4 has a *L. sativa* origin when a plant is phenotypically susceptible. This confirms that the *N. ribisnigri* biotype Nr:1 resistant *L. serriola* accessions indeed are the donor of the resistant phenotype observed in the *L. serriola* x *L. sativa* mapping populations.

Example 2

Validation of Resistance Conferred by Loci Identified on Chromosomes 4 and 8 When Introgressed Into Different Lettuce Backgrounds To determine the efficacy *N. ribisnigri* biotype Nr:1 resistance loci identified in *L. serriola*, non-choice assays using a fixed number of aphids were performed on *L. sativa* plants where either the locus on chromosome 8 was introgressed into the plant or both the locus on chromosome 8 and the locus on chromosome 4 were introgressed into the plant. The *L. sativa* plants were either Batavia or Butterhead varieties. Plants of the Batavia lettuce background also contained the Nr gene, which provides resistance against *N. ribisnigri* biotype Nr:0, while the Butterhead lettuce plants did not. Two different *L. serriola* accessions were used as resistance donors in order to investigate the uniformity of resistance to *N. ribisnigri* biotype Nr:1 across resistant *L. serriola* accessions. A randomized complete design with 5 replications and 3-4 plants/replication was used. Susceptible (Batavia and Butterhead parental lines) and resistant (the two *L. serriola* accessions used as donors) controls were placed in every replication. Seeds were initially sown in rock wool flats and transplanted into 12 cm pots with soil at 5 weeks. At 8 weeks, the plants were inoculated with 5 similarly-sized aphids of biotype Nr:1 and covered with a perforated bag to keep the aphids confined to the plant. The trial was scored once at 21 days post inoculation by counting the number of aphids on each plant. Resistance was determined as the number of aphids present on each plant 21 days after inoculation, where a low aphid count represented a high level of resistance.

Figure 2:
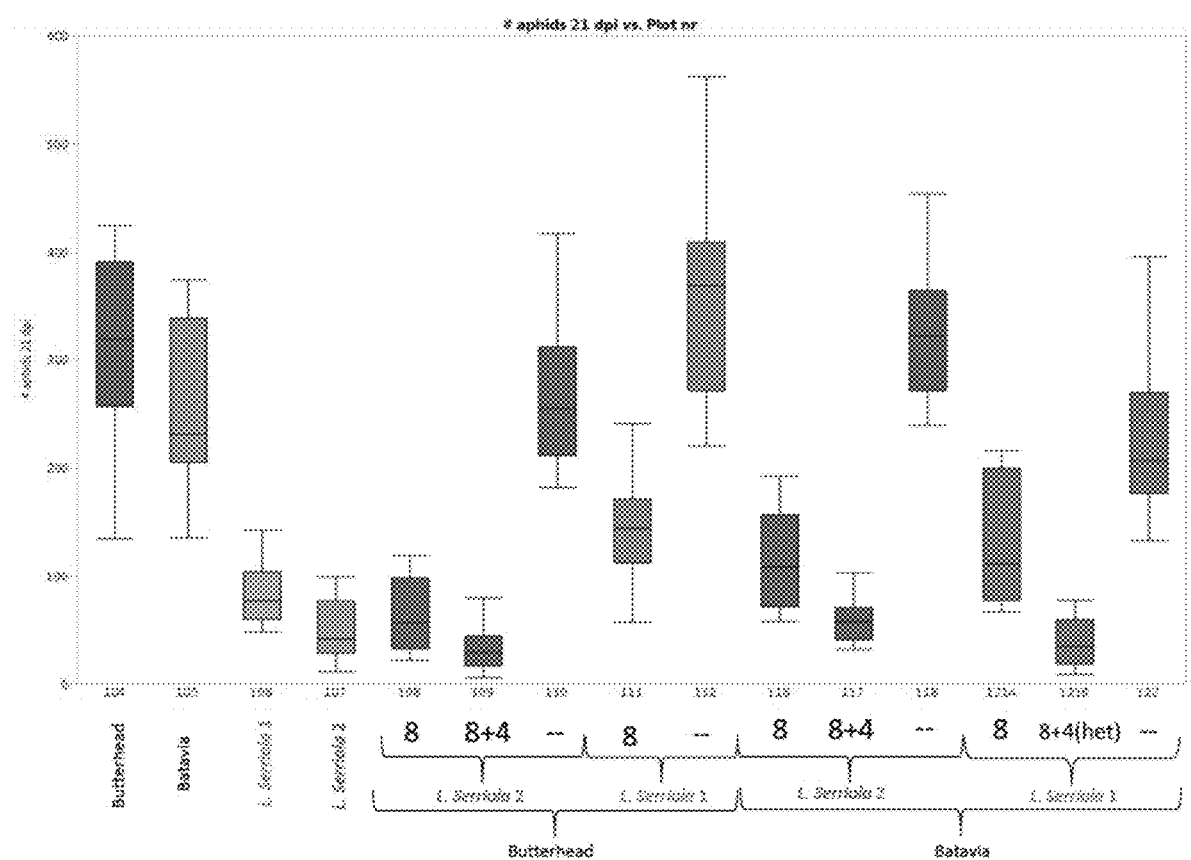
FIG. 2: Shows the results of the *Nasonovia ribisnigri* biotype Nr:1 resistance assays. The resistance loci identified from QTL mapping were introgressed from two different *L. serriola* lines (shown as "*L. serriola* 1" and "*L. serriola* 2") into two different elite lettuce varieties (Butterhead and Batavia) and plants were inoculated with a fixed number of aphids. Resistance is expressed as the number of aphids counted on each plant 21 days post infection (dpi). Unless indicated otherwise the introgressions were fixed in the tested plants.

It was observed that homozygous deployment of the resistance locus on chromosome 8 conferred robust resistance to *N. ribisnigri* biotype Nr:1 when introgressed into both *L. sativa* lettuce types (FIG. 2). Furthermore, the presence of the resistance locus on chromosome 4 in either a homozygous or heterozygous configuration further improved the resistance to *N. ribisnigri* biotype Nr:1 conferred by the locus on chromosome 8 in both *L. sativa* lettuce types. The resistance conferred by loci introgressed into both *L. sativa* lettuce types from the two *L. serriola* accessions was comparable (FIG. 2). These results confirm that the same level of resistance can be obtained from multiple *L. serriola* donors.

What is claimed is:

1. An elite *Lactuca sativa* plant comprising at least a first recombinant chromosomal segment on chromosome 8 from *Lactuca serriola* on chromosome 8, wherein said recombinant chromosomal segment comprises an allele conferring resistance to *Nasonovia ribisnigri* biotype Nr:1 relative to a plant lacking said recombinant chromosomal segment, and wherein said first recombinant chromosomal segment comprises a marker locus selected from the group consisting of marker locus M1 (SEQ ID NO: 26), marker locus M2 (SEQ ID NO: 16), marker locus M4 (SEQ ID NO: 46), marker locus M5 (SEQ ID NO: 11), marker locus M7 (SEQ ID NO: 21), marker locus M8 (SEQ ID NO: 41), marker locus M10 (SEQ ID NO: 36), and marker locus M11 (SEQ ID NO: 31).

2. The plant of claim 1, wherein said *Nasonovia ribisnigri* biotype Nr:1 resistance allele is located between 106,984,777 bp and 136,545,853 bp on chromosome 8 of the public *Lactuca sativa* reference genome Lsat_Salinas_v7.

3. A plant part of the plant of claim 1, wherein said plant part comprises said first recombinant chromosomal segment.

4. The plant part of claim 3, wherein said plant part is a cell, a seed, a root, a stem, a leaf, a head, a flower, or pollen.

5. A seed that produces the plant of claim 1.

6. The plant of claim 1, wherein the plant is homozygous for said recombinant chromosomal segment.

7. The plant of claim 1, wherein said plant further comprises a second recombinant chromosomal segment on chromosome 4, wherein said second recombinant chromosomal segment comprises an allele conferring further improved resistance to *Nasonovia ribisnigri* biotype Nr:1 relative to a plant lacking said second recombinant chromosomal segment.

8. The plant of claim 7, wherein second recombinant chromosomal segment comprises a marker selected from the group consisting of marker locus M13 (SEQ ID NO: 61), marker locus M14 (SEQ ID NO: 66), marker locus M15 (SEQ ID NO: 67), marker locus M16 (SEQ ID NO: 68), marker locus M17 (SEQ ID NO: 69), marker locus M18 (SEQ ID NO: 70), marker locus M19 (SEQ ID NO: 75), marker locus M20 (SEQ ID NO: 76), marker locus M21 (SEQ ID NO: 81), marker locus M22 (SEQ ID NO: 86), and marker locus M23 (SEQ ID NO: 91) on chromosome 4.

9. A plant part of the plant of claim 7, wherein said plant part comprises said first and said second recombinant chromosomal segments.

10. The plant part of claim 9, wherein said plant part is a cell, a seed, a root, a stem, a leaf, a head, a flower, or pollen.

11. A seed that produces the plant of claim 7.

12. The *Lactuca sativa* plant of claim 7, wherein a representative sample of seed comprising said first and said second recombinant chromosomal segments has been deposited under ATCC Accession No. PTA-126067.

13. A method for producing an elite Lactuca sativa plant with improved resistance to *Nasonovia ribisnigri* biotype Nr:1 comprising introgressing into said plant a *Nasonovia ribisnigri* biotype Nr:1 resistance allele from chromosome 8 within a recombinant chromosomal segment flanked in the genome of said plant by marker locus M5 (SEQ ID NO: 11) and marker locus M4 (SEQ ID NO: 46) on chromosome 8, wherein said introgressed *Nasonovia ribisnigri* biotype Nr:1 resistance allele confers to said plant resistance to *Nasonovia ribisnigri* biotype Nr:1 relative to a plant lacking said allele.

14. The method of claim 13, wherein said introgressing comprises:
  a) crossing a plant comprising said recombinant chromosomal segment with itself or with a second *Lactuca sativa* plant of a different genotype to produce one or more progeny plants; and b) selecting a progeny plant comprising said recombinant chromosomal segment.

15. The method of claim 14, wherein selecting a progeny plant comprises detecting nucleic acids comprising marker locus M1 (SEQ ID NO: 26), marker locus M2 (SEQ ID NO: 16), marker locus M4 (SEQ ID NO: 46), marker locus M5 (SEQ ID NO: 11), marker locus M7 (SEQ ID NO: 21), marker locus M8 (SEQ ID NO: 41), marker locus M10 (SEQ ID NO: 36), or marker locus M11 (SEQ ID NO: 31).

16. The method of claim 14, wherein the progeny plant is an F2-F6 progeny plant.

17. The method of claim 13, wherein said introgressing comprises backcrossing, marker-assisted selection or assaying for said resistance to *Nasonovia ribisnigri* biotype Nr:1.

18. The method of claim 17, wherein said backcrossing comprises from 2-7 generations of backcrosses.

19. A *Lactuca sativa* plant obtainable by the method of claim 13.

20. The method of claim 13, wherein said plant further comprises a second introgressed *Nasonovia ribisnigri* biotype Nr:1 resistance allele within a recombinant chromosomal segment flanked in the genome of said plant by marker locus M5 (SEQ ID NO: 11) and marker locus M4 (SEQ ID NO: 46) on chromosome 8 or by marker locus M13 (SEQ ID NO: 61) and marker locus M23 (SEQ ID NO: 91) on chromosome 4.

21. A method of selecting a *Lactuca sativa* plant exhibiting resistance to *Nasonovia ribisnigri* biotype Nr:1, comprising:

a) crossing the *Lactuca sativa* plant of claim 1 with itself or with a second *Lactuca sativa* plant of a different genotype to produce one or more progeny plants; and b) selecting a progeny plant comprising said *Nasonovia ribisnigri* biotype Nr:1 resistance allele.

22. The method of claim 21, wherein selecting said progeny plant comprises detecting a marker locus genetically linked to said *Nasonovia ribisnigri* biotype Nr:1 resistance allele.

23. The method of claim 22, wherein selecting said progeny plant comprises detecting a marker locus within or genetically linked to a chromosomal segment flanked in the genome of said plant by marker locus M5 (SEQ ID NO: 11) and marker locus M4 (SEQ ID NO: 46) on chromosome 8.

24. The method of claim 22, wherein selecting a progeny comprises detecting nucleic acids comprising marker locus M1 (SEQ ID NO: 26), marker locus M2 (SEQ ID NO: 16 ), marker locus M4 (SEQ ID NO: 46), marker locus M5 (SEQ ID NO: 11), marker locus M7 (SEQ ID NO: 21), marker locus M8 (SEQ ID NO: 41), marker locus M10 (SEQ ID NO: 36), or marker locus M11 (SEQ ID NO: 31).

25. The method of claim 21, wherein said progeny plant is an F2-F6 progeny plant.

26. The method of claim 21, wherein producing said progeny plant comprises backcrossing.

* * * * *

SEQUENCE LISTING

<160> NUMBER OF SEQ ID NOS: 95

<210> SEQ ID NO 1
<211> LENGTH: 121
<212> TYPE: DNA
<213> ORGANISM: Lactuca serriola

<400> SEQUENCE: 1

```
acaagttgaa atcactatat ggttgtggta ttaattccct tgataatcta gcaaatgaag      60
tcaatggaaa ttcacagtca acactcgaac atcttaattc tcaagtctcc caaaattctt     120
c                                                                     121
```

<210> SEQ ID NO 2

```
<211> LENGTH: 31
<212> TYPE: DNA
<213> ORGANISM: Artificial Sequence
<220> FEATURE:
<223> OTHER INFORMATION: Primer

<400> SEQUENCE: 2
cactatatgg ttgtggtatt aattcccttg a                                    31

<210> SEQ ID NO 3
<211> LENGTH: 27
<212> TYPE: DNA
<213> ORGANISM: Artificial Sequence
<220> FEATURE:
<223> OTHER INFORMATION: Primer

<400> SEQUENCE: 3
gggagacttg agaattaaga tgttcga                                         27

<210> SEQ ID NO 4
<211> LENGTH: 20
<212> TYPE: DNA
<213> ORGANISM: Artificial Sequence
<220> FEATURE:
<223> OTHER INFORMATION: Probe

<400> SEQUENCE: 4
tgaatttcca ttgacttcat                                                 20

<210> SEQ ID NO 5
<211> LENGTH: 18
<212> TYPE: DNA
<213> ORGANISM: Artificial Sequence
<220> FEATURE:
<223> OTHER INFORMATION: Probe

<400> SEQUENCE: 5
aatttccatt ggcttcat                                                   18

<210> SEQ ID NO 6
<211> LENGTH: 121
<212> TYPE: DNA
<213> ORGANISM: Lactuca serriola

<400> SEQUENCE: 6
gagatatgac cgattaagga gtatttctgg aaggattcag acggttgttg gtgatttggc     60
aacacaagga gagaggcttc agtctttgct gagctggcga gatcccagag caactgcatt    120
g                                                                    121

<210> SEQ ID NO 7
<211> LENGTH: 27
<212> TYPE: DNA
<213> ORGANISM: Artificial Sequence
<220> FEATURE:
<223> OTHER INFORMATION: Primer

<400> SEQUENCE: 7
accgattaag gagtatttct ggaagga                                         27

<210> SEQ ID NO 8
<211> LENGTH: 22
<212> TYPE: DNA
<213> ORGANISM: Artificial Sequence
<220> FEATURE:
<223> OTHER INFORMATION: Primer
```

<400> SEQUENCE: 8
cagcaaagac tgaagcctct ct                                              22

<210> SEQ ID NO 9
<211> LENGTH: 19
<212> TYPE: DNA
<213> ORGANISM: Artificial Sequence
<220> FEATURE:
<223> OTHER INFORMATION: Probe

<400> SEQUENCE: 9
tggtgatttg gcaacacaa                                                  19

<210> SEQ ID NO 10
<211> LENGTH: 20
<212> TYPE: DNA
<213> ORGANISM: Artificial Sequence
<220> FEATURE:
<223> OTHER INFORMATION: Probe

<400> SEQUENCE: 10
ttggtgattt ggctacacaa                                                 20

<210> SEQ ID NO 11
<211> LENGTH: 121
<212> TYPE: DNA
<213> ORGANISM: Lactuca serriola
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (100)..(100)
<223> OTHER INFORMATION: n is a, c, g, or t

<400> SEQUENCE: 11
cacnccatac tctacctcta caccataact actacaatca gacgccgccg taaacaacca     60
cctatcggca ttcaactccg tcgtcgactc cgttcgcttn gcaaaccggc ctttgatcct    120
c                                                                    121

<210> SEQ ID NO 12
<211> LENGTH: 18
<212> TYPE: DNA
<213> ORGANISM: Artificial Sequence
<220> FEATURE:
<223> OTHER INFORMATION: Primer

<400> SEQUENCE: 12
aatcagacgc cgccgtaa                                                   18

<210> SEQ ID NO 13
<211> LENGTH: 19
<212> TYPE: DNA
<213> ORGANISM: Artificial Sequence
<220> FEATURE:
<223> OTHER INFORMATION: Primer

<400> SEQUENCE: 13
gagtcgacga cggagttga                                                  19

<210> SEQ ID NO 14
<211> LENGTH: 18
<212> TYPE: DNA

```
<213> ORGANISM: Artificial Sequence
<220> FEATURE:
<223> OTHER INFORMATION: Probe

<400> SEQUENCE: 14
atgccgatag gtggttgt                                                        18

<210> SEQ ID NO 15
<211> LENGTH: 17
<212> TYPE: DNA
<213> ORGANISM: Artificial Sequence
<220> FEATURE:
<223> OTHER INFORMATION: Probe

<400> SEQUENCE: 15
tgccgatagc tggttgt                                                         17

<210> SEQ ID NO 16
<211> LENGTH: 201
<212> TYPE: DNA
<213> ORGANISM: Lactuca serriola

<400> SEQUENCE: 16
cattgtcagt tgtgccctag gccatttcac agtccctttg atgcaagatt ccttaatggc          60
agacattttg ccactctaaa cgtccaaatt tgtgatttca tatcctcgaa acttcaagtc         120
tgttggctca attctggagg aaatgttgga aaaggttcct cttgacaata caatattgag         180
ggagtatcag aagttaccat c                                                   201

<210> SEQ ID NO 17
<211> LENGTH: 24
<212> TYPE: DNA
<213> ORGANISM: Artificial Sequence
<220> FEATURE:
<223> OTHER INFORMATION: Primer

<400> SEQUENCE: 17
gccactctaa acgtccaaat ttgt                                                 24

<210> SEQ ID NO 18
<211> LENGTH: 25
<212> TYPE: DNA
<213> ORGANISM: Artificial Sequence
<220> FEATURE:
<223> OTHER INFORMATION: Primer

<400> SEQUENCE: 18
cagaattgag ccaacagact tgaag                                                25

<210> SEQ ID NO 19
<211> LENGTH: 18
<212> TYPE: DNA
<213> ORGANISM: Artificial Sequence
<220> FEATURE:
<223> OTHER INFORMATION: Probe

<400> SEQUENCE: 19
tttcgaggat atgaaatc                                                        18

<210> SEQ ID NO 20
<211> LENGTH: 15
<212> TYPE: DNA
<213> ORGANISM: Artificial Sequence
<220> FEATURE:
<223> OTHER INFORMATION: Probe
```

<400> SEQUENCE: 20
cgaggatctg aaatc                                              15

<210> SEQ ID NO 21
<211> LENGTH: 121
<212> TYPE: DNA
<213> ORGANISM: Lactuca serriola
<220> FEATURE:
<221> NAME/KEY: misc_feature
<222> LOCATION: (16)..(16)
<223> OTHER INFORMATION: n is a, c, g, or t

<400> SEQUENCE: 21
tactccaata gggggngggc gggtcaaccc gcccgataga agaaaccta atagcccaaa      60 tatattcaat gggcccactt ctcaccccaa agaacaatct gacttggtca acgtctttc    120 c                                                                   121

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
cccgcccgat agaagaaacc                                         20

<210> SEQ ID NO 23
<211> LENGTH: 19
<212> TYPE: DNA
<213> ORGANISM: Artificial Sequence
<220> FEATURE:
<223> OTHER INFORMATION: Primer

<400> SEQUENCE: 23
ggtgagaagt gggcccatt                                          19

<210> SEQ ID NO 24
<211> LENGTH: 18
<212> TYPE: DNA
<213> ORGANISM: Artificial Sequence
<220> FEATURE:
<223> OTHER INFORMATION: Probe

<400> SEQUENCE: 24
aatagcccaa atatattc                                           18

<210> SEQ ID NO 25
<211> LENGTH: 16
<212> TYPE: DNA
<213> ORGANISM: Artificial Sequence
<220> FEATURE:
<223> OTHER INFORMATION: Probe

<400> SEQUENCE: 25
tagcccaaac atattc                                             16

<210> SEQ ID NO 26
<211> LENGTH: 201
<212> TYPE: DNA
<213> ORGANISM: Lactuca serriola

<400> SEQUENCE: 26

```
gtcctgtcct gtaaagtgtc aaccgactta ccctttttaat ggttcaacag attcccacac    60
tcgaggctcc gcatctttgt ccttacatat cttaaaaaac aaaaaataaa aataaaaatt   120
agaactttga aaagaaaaaa acgtgtattt gttgttaata tcaaatttc atacttggag    180 tccagaaaca ctatcggttg c                                              201
```

<210> SEQ ID NO 27
<211> LENGTH: 21
<212> TYPE: DNA
<213> ORGANISM: Artificial Sequence
<220> FEATURE:
<223> OTHER INFORMATION: Primer

<400> SEQUENCE: 27

```
ggctccgcat ctttgtcctt a                                              21
```

<210> SEQ ID NO 28
<211> LENGTH: 34
<212> TYPE: DNA
<213> ORGANISM: Artificial Sequence
<220> FEATURE:
<223> OTHER INFORMATION: Primer

<400> SEQUENCE: 28

```
caacaaatac acgttttttt cttttcaaag ttct                                34
```

<210> SEQ ID NO 29
<211> LENGTH: 23
<212> TYPE: DNA
<213> ORGANISM: Artificial Sequence
<220> FEATURE:
<223> OTHER INFORMATION: Probe

<400> SEQUENCE: 29

```
catatcttta aaacaaaaa ata                                             23
```

<210> SEQ ID NO 30
<211> LENGTH: 20
<212> TYPE: DNA
<213> ORGANISM: Artificial Sequence
<220> FEATURE:
<223> OTHER INFORMATION: Probe

<400> SEQUENCE: 30

```
atctttaaaa accaaaaata                                                20
```

<210> SEQ ID NO 31
<211> LENGTH: 432
<212> TYPE: DNA
<213> ORGANISM: Lactuca serriola
<220> FEATURE:
<221> NAME/KEY: misc_feature
<222> LOCATION: (273)..(273)
<223> OTHER INFORMATION: n is a, c, g, or t
<220> FEATURE:
<221> NAME/KEY: misc_feature
<222> LOCATION: (298)..(298)
<223> OTHER INFORMATION: n is a, c, g, or t
<220> FEATURE:
<221> NAME/KEY: misc_feature
<222> LOCATION: (348)..(348)
<223> OTHER INFORMATION: n is a, c, g, or t

<400> SEQUENCE: 31

```
cgaaggacac gagcttgggt ctggtttgat cggaaaggct caagggtatt atgtatcgag    60
ttccatagat gggaagagtc agacgatggc gtttactgtg atgtttatgc acgggagtta   120
```

```
tattgatagt ttgagcttta tgggggttca ccggagtgcg gtggcggagt cccagctggc    180
ggtgatgggt ggcaccggga agtatgtgaa tgctaaaggg catgcggtgg tgaagacttt    240 tcagggaca aaccagcaga ataatgatgg aantgagaca ctgcttcagt ttcatgtnta     300
tcttgcgtat tagtttgtat aagtctatgt gtgtttggtt tctatttnta tgctttccat   360
gtttatgtga tgttatgaaa atttgtgtgt gaaatacaaa agaatttaac aatttctact   420
tttcccggag ag                                                       432
```

```
<210> SEQ ID NO 32
<211> LENGTH: 17
<212> TYPE: DNA
<213> ORGANISM: Artificial Sequence
<220> FEATURE:
<223> OTHER INFORMATION: Primer

<400> SEQUENCE: 32
agtcccagct ggcggtg                                                   17
```

```
<210> SEQ ID NO 33
<211> LENGTH: 24
<212> TYPE: DNA
<213> ORGANISM: Artificial Sequence
<220> FEATURE:
<223> OTHER INFORMATION: Primer

<400> SEQUENCE: 33
ccatcattat tctgctggtt tgtc                                           24
```

```
<210> SEQ ID NO 34
<211> LENGTH: 14
<212> TYPE: DNA
<213> ORGANISM: Artificial Sequence
<220> FEATURE:
<223> OTHER INFORMATION: Probe

<400> SEQUENCE: 34
cttcccggtg ccac                                                      14
```

```
<210> SEQ ID NO 35
<211> LENGTH: 14
<212> TYPE: DNA
<213> ORGANISM: Artificial Sequence
<220> FEATURE:
<223> OTHER INFORMATION: Probe

<400> SEQUENCE: 35
cttcccagtg ccac                                                      14
```

```
<210> SEQ ID NO 36
<211> LENGTH: 121
<212> TYPE: DNA
<213> ORGANISM: Lactuca serriola

<400> SEQUENCE: 36
agaggccaat gtgttgaaga tcaggaaagt ttatgatgca ttttggctg aatttcctct     60 ctgttatggc tactggaaga agtatgctga tcatgaagca agattggggt ctattgataa   120
a                                                                   121
```

```
<210> SEQ ID NO 37
<211> LENGTH: 25
<212> TYPE: DNA
```

```
<213> ORGANISM: Artificial Sequence
<220> FEATURE:
<223> OTHER INFORMATION: Primer

<400> SEQUENCE: 37
aaagtttatg atgcattttt ggctg                                          25

<210> SEQ ID NO 38
<211> LENGTH: 26
<212> TYPE: DNA
<213> ORGANISM: Artificial Sequence
<220> FEATURE:
<223> OTHER INFORMATION: Primer

<400> SEQUENCE: 38
ttgcttcatg atcagcatac ttcttc                                         26

<210> SEQ ID NO 39
<211> LENGTH: 18
<212> TYPE: DNA
<213> ORGANISM: Artificial Sequence
<220> FEATURE:
<223> OTHER INFORMATION: Probe

<400> SEQUENCE: 39
atttcctctc tgttatgg                                                  18

<210> SEQ ID NO 40
<211> LENGTH: 17
<212> TYPE: DNA
<213> ORGANISM: Artificial Sequence
<220> FEATURE:
<223> OTHER INFORMATION: Probe

<400> SEQUENCE: 40
tttcctctgt gttatgg                                                   17

<210> SEQ ID NO 41
<211> LENGTH: 2003
<212> TYPE: DNA
<213> ORGANISM: Lactuca serriola
<220> FEATURE:
<221> NAME/KEY: misc_feature
<222> LOCATION: (52)..(52)
<223> OTHER INFORMATION: n is a, c, g, or t
<220> FEATURE:
<221> NAME/KEY: misc_feature
<222> LOCATION: (178)..(178)
<223> OTHER INFORMATION: n is a, c, g, or t
<220> FEATURE:
<221> NAME/KEY: misc_feature
<222> LOCATION: (211)..(211)
<223> OTHER INFORMATION: n is a, c, g, or t
<220> FEATURE:
<221> NAME/KEY: misc_feature
<222> LOCATION: (232)..(232)
<223> OTHER INFORMATION: n is a, c, g, or t
<220> FEATURE:
<221> NAME/KEY: misc_feature
<222> LOCATION: (386)..(386)
<223> OTHER INFORMATION: n is a, c, g, or t
<220> FEATURE:
<221> NAME/KEY: misc_feature
<222> LOCATION: (648)..(648)
<223> OTHER INFORMATION: n is a, c, g, or t
<220> FEATURE:
<221> NAME/KEY: misc_feature
<222> LOCATION: (662)..(662)
<223> OTHER INFORMATION: n is a, c, g, or t
<220> FEATURE:
<221> NAME/KEY: misc_feature
```

-continued

```
<222> LOCATION: (690)..(690)
<223> OTHER INFORMATION: n is a, c, g, or t
<220> FEATURE:
<221> NAME/KEY: misc_feature
<222> LOCATION: (733)..(733)
<223> OTHER INFORMATION: n is a, c, g, or t
<220> FEATURE:
<221> NAME/KEY: misc_feature
<222> LOCATION: (912)..(912)
<223> OTHER INFORMATION: n is a, c, g, or t
<220> FEATURE:
<221> NAME/KEY: misc_feature
<222> LOCATION: (936)..(936)
<223> OTHER INFORMATION: n is a, c, g, or t
<220> FEATURE:
<221> NAME/KEY: misc_feature
<222> LOCATION: (991)..(991)
<223> OTHER INFORMATION: n is a, c, g, or t
<220> FEATURE:
<221> NAME/KEY: misc_feature
<222> LOCATION: (1015)..(1015)
<223> OTHER INFORMATION: n is a, c, g, or t
<220> FEATURE:
<221> NAME/KEY: misc_feature
<222> LOCATION: (1033)..(1033)
<223> OTHER INFORMATION: n is a, c, g, or t
<220> FEATURE:
<221> NAME/KEY: misc_feature
<222> LOCATION: (1052)..(1052)
<223> OTHER INFORMATION: n is a, c, g, or t
<220> FEATURE:
<221> NAME/KEY: misc_feature
<222> LOCATION: (1062)..(1062)
<223> OTHER INFORMATION: n is a, c, g, or t
<220> FEATURE:
<221> NAME/KEY: misc_feature
<222> LOCATION: (1099)..(1099)
<223> OTHER INFORMATION: n is a, c, g, or t
<220> FEATURE:
<221> NAME/KEY: misc_feature
<222> LOCATION: (1169)..(1169)
<223> OTHER INFORMATION: n is a, c, g, or t
<220> FEATURE:
<221> NAME/KEY: misc_feature
<222> LOCATION: (1182)..(1182)
<223> OTHER INFORMATION: n is a, c, g, or t
<220> FEATURE:
<221> NAME/KEY: misc_feature
<222> LOCATION: (1213)..(1213)
<223> OTHER INFORMATION: n is a, c, g, or t
<220> FEATURE:
<221> NAME/KEY: misc_feature
<222> LOCATION: (1238)..(1238)
<223> OTHER INFORMATION: n is a, c, g, or t
<220> FEATURE:
<221> NAME/KEY: misc_feature
<222> LOCATION: (1244)..(1244)
<223> OTHER INFORMATION: n is a, c, g, or t
<220> FEATURE:
<221> NAME/KEY: misc_feature
<222> LOCATION: (1252)..(1252)
<223> OTHER INFORMATION: n is a, c, g, or t
<220> FEATURE:
<221> NAME/KEY: misc_feature
<222> LOCATION: (1265)..(1265)
<223> OTHER INFORMATION: n is a, c, g, or t
<220> FEATURE:
<221> NAME/KEY: misc_feature
<222> LOCATION: (1283)..(1283)
<223> OTHER INFORMATION: n is a, c, g, or t
<220> FEATURE:
<221> NAME/KEY: misc_feature
<222> LOCATION: (1329)..(1329)
<223> OTHER INFORMATION: n is a, c, g, or t
<220> FEATURE:
<221> NAME/KEY: misc_feature
<222> LOCATION: (1344)..(1344)
<223> OTHER INFORMATION: n is a, c, g, or t
<220> FEATURE:
```

<220> FEATURE:
<221> NAME/KEY: misc_feature
<222> LOCATION: (1690)..(1690)
<223> OTHER INFORMATION: n is a, c, g, or t
<220> FEATURE:
<221> NAME/KEY: misc_feature
<222> LOCATION: (1833)..(1833)
<223> OTHER INFORMATION: n is a, c, g, or t

<400> SEQUENCE: 41

```
cgggggctag tgagttacgt tccgtcgtac ctcgccggaa acattcact gncgccataa      60
actacggtgt tgcagaaata gttgctctag gtgtgaagga aagttatcac tcggtggtta    120
ttggatctat aagcttgcat cttt gaatct ctgttcgcac ttttcacttt ctctctcnag   180
aaaatgagga cggatatggt gaataggtgt ntgagtttat cacaacattc gnttccacaa   240
tcaccttctt cttcgtcttc tccttcttct tcattgcaaa ctctagcctc tgcaatctct   300
tcaccgtcag caaaacgacg gtgtttgacc caccgcgcac tggcttaccg ctacgttcac   360
cggtcggcga tatttgggac gaagcngaag agatccgacc catctagaga gccgcagctt   420
atccaacgca ccgtctccgc cagcttagat gcagagtttt cggatgaaga attctcaaag   480
aaaattcgag aactagctct ccagtttcaa gtttccgacg aatttggcaa taagagaag    540
tatgacggtt tagcattgga attggaattg catcggaga gccagagccc atttgctggt    600
ttgaagatgg aagtgcctga ctggccaggg gatatgattc cggcgagnat tgagcgaaag   660
gngaacagcg ttgagttgcc attttcattn cgaattatca agaggaagaa acaatggcag   720
gagggaataa ganacgcagg tgaatctgcc tattgttcag taaaaaaagc tttctcttca   780
atggtgttca taatccgaga gcttcaaagc tacacacttc aaatgagaga cttttatac    840
tacgaagatt tacaggggat tcttgtgaga gttcagcaag aaatgaacgc atctttcgtc   900
tggttgttcc ancaagtctt ttcccaaacc cctacnttaa tggtgtacgt gatgattctt   960
ttagccaatt acagtgtata ttcaatgtca nacaatatcg cactcgcggc gccgncacct  1020
cccgccaccg tanagtcgat tacagaacac cnaagtgaaa cnaaattcga ttcttcatca  1080
gtcaaaacgt tttctgtana ttcaggtggg aaaaccacct caatcggcgg aaacaacggc  1140
ggcggtggga aattcagggc agttgctanc gggacagacg gngacgggag atttgatgga  1200
tctataactt cancgtcatc aatcgtaaac ccgacaanga ctancgagga gncggtttcg  1260
ggtcnagcga gtaaggataa tgnatgggag tcatggaatt cgattgtgga tgaagctgac  1320
agaatgcang gtgtgatcgg aganaacggc gatctggatc atgaaactat gaaaagattt  1380
gtttctccgg tgactgtgaa aatcgaggaa gaagatacag aagatcactc caaaacagag  1440
cttctttatc aaacgggtct ctcacaagaa cccgacaacc cgcttcttct tgcgaattac  1500
gcccagtttc tgtacctcgt tacacgagat tacgatagag ctgaggatta cttcaaaaga  1560
gcttcaatgg tggaacctaa agacgcagaa gcacttaaca aatacgcaag cttttatgg   1620
caagttcgaa aagacttgtg ggctgctgaa gagacttatt tggaagccat ttctgctgat  1680
cctacaaacn ctttttatgc tgcaaattat gcacatttct tatggagcac cggtggagaa  1740
gacacttgtt tccctcttga ctcgccggga aatatgttct ccgacgaagt gtgaattaac  1800
caccggcgtc ggagacgtgg gtttaactta ganagttggg acatgataat aaacgagatt  1860
tgagcgggaa gtggtggtgg atggttgaaa ggtggaatat gataatcttg attttccggc  1920
gaaaggtggt ttgaagttgt caaaaattgt aattaagttt tgttgatatc aaattataaa  1980
tgaaaatgaa tttaggtgaa acg                                           2003
```

<210> SEQ ID NO 42
<211> LENGTH: 21
<212> TYPE: DNA
<213> ORGANISM: Artificial Sequence
<220> FEATURE:
<223> OTHER INFORMATION: Primer

<400> SEQUENCE: 42
catctagaga gccgcagctt a                                            21

<210> SEQ ID NO 43
<211> LENGTH: 26
<212> TYPE: DNA
<213> ORGANISM: Artificial Sequence
<220> FEATURE:
<223> OTHER INFORMATION: Primer

<400> SEQUENCE: 43
attcttcatc cgaaaactct gcatct                                       26

<210> SEQ ID NO 44
<211> LENGTH: 16
<212> TYPE: DNA
<213> ORGANISM: Artificial Sequence
<220> FEATURE:
<223> OTHER INFORMATION: Probe

<400> SEQUENCE: 44
tccaacgcac cgtctc                                                  16

<210> SEQ ID NO 45
<211> LENGTH: 14
<212> TYPE: DNA
<213> ORGANISM: Artificial Sequence
<220> FEATURE:
<223> OTHER INFORMATION: Probe

<400> SEQUENCE: 45
caacgcgccg tctc                                                    14

<210> SEQ ID NO 46
<211> LENGTH: 201
<212> TYPE: DNA
<213> ORGANISM: Lactuca serriola

<400> SEQUENCE: 46
tggcttagga gatgggaaag aacgaaggtc aactgctcac catagaactc ttgctaaaca        60
ggttgattcg tcaccatcaa attaaacatg agttcacaat tctggggtag ggatctgatt       120
ttcctagatg ataatgacga gaatgatggt gattcaagag acctatgctt tggggaaagg       180
gtctatggga tttttttattt t                                              201

<210> SEQ ID NO 47
<211> LENGTH: 25
<212> TYPE: DNA
<213> ORGANISM: Artificial Sequence
<220> FEATURE:
<223> OTHER INFORMATION: Primer

<400> SEQUENCE: 47
gctaaacagg ttgattcgtc accat                                        25

<210> SEQ ID NO 48
<211> LENGTH: 29
<212> TYPE: DNA

```
<213> ORGANISM: Artificial Sequence
<220> FEATURE:
<223> OTHER INFORMATION: Primer

<400> SEQUENCE: 48
accatcattc tcgtcattat catctagga                                         29

<210> SEQ ID NO 49
<211> LENGTH: 14
<212> TYPE: DNA
<213> ORGANISM: Artificial Sequence
<220> FEATURE:
<223> OTHER INFORMATION: Probe

<400> SEQUENCE: 49
accccagaat tgtg                                                          14

<210> SEQ ID NO 50
<211> LENGTH: 14
<212> TYPE: DNA
<213> ORGANISM: Artificial Sequence
<220> FEATURE:
<223> OTHER INFORMATION: Probe

<400> SEQUENCE: 50
accccaggat tgtg                                                          14

<210> SEQ ID NO 51
<211> LENGTH: 201
<212> TYPE: DNA
<213> ORGANISM: Lactuca serriola

<400> SEQUENCE: 51
aaaagaattt gctaaccctg aagctaaaat aaaaggtctt tcatgtctcc actgttcaaa        60
agttcatttt tgtcatcttc gtctgccaat tccttcaccg cagaaaagaa gcaaagatca      120 ccgttttgt ctattcttgt gtatcttcta ttgaaaaaac atgatgcaaa gtaagcaatc       180
aatcaacttt tttttattc a                                                  201

<210> SEQ ID NO 52
<211> LENGTH: 23
<212> TYPE: DNA
<213> ORGANISM: Artificial Sequence
<220> FEATURE:
<223> OTHER INFORMATION: Primer

<400> SEQUENCE: 52
tgtcatcttc gtctgccaat tcc                                               23

<210> SEQ ID NO 53
<211> LENGTH: 28
<212> TYPE: DNA
<213> ORGANISM: Artificial Sequence
<220> FEATURE:
<223> OTHER INFORMATION: Primer

<400> SEQUENCE: 53
acacaagaat agacaaaaac ggtgatct                                          28

<210> SEQ ID NO 54
<211> LENGTH: 20
<212> TYPE: DNA
<213> ORGANISM: Artificial Sequence
<220> FEATURE:
<223> OTHER INFORMATION: Probe
```

<400> SEQUENCE: 54 tgcttcttttt ctgcggtgaa                                              20

<210> SEQ ID NO 55
<211> LENGTH: 21
<212> TYPE: DNA
<213> ORGANISM: Artificial Sequence
<220> FEATURE:
<223> OTHER INFORMATION: Probe

<400> SEQUENCE: 55 ttgcttctttt tctacggtga a                                            21

<210> SEQ ID NO 56
<211> LENGTH: 297
<212> TYPE: DNA
<213> ORGANISM: Lactuca serriola
<220> FEATURE:
<221> NAME/KEY: misc_feature
<222> LOCATION: (66)..(66)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (143)..(143)
<223> OTHER INFORMATION: n is a, c, g, or t
<220> FEATURE:
<221> NAME/KEY: misc_feature
<222> LOCATION: (153)..(155)
<223> OTHER INFORMATION: n is a, c, g, or t
<220> FEATURE:
<221> NAME/KEY: misc_feature
<222> LOCATION: (174)..(174)
<223> OTHER INFORMATION: n is a, c, g, or t
<220> FEATURE:
<221> NAME/KEY: misc_feature
<222> LOCATION: (243)..(243)
<223> OTHER INFORMATION: n is a, c, g, or t
<220> FEATURE:
<221> NAME/KEY: misc_feature
<222> LOCATION: (247)..(247)
<223> OTHER INFORMATION: n is a, c, g, or t

<400> SEQUENCE: 56
gctaaggcac agcctgattt agttgcagat gaaaacgatg atgaattact cacagaaaaa      60
gatagnttcg aggaggtgaa ggatatggaa catgcaaagc ngcaagaatc tagcccaagt     120
gatgctaaaa actctatcaa agnggaagaa cannntgatg atgtttgtat gccnttaaaa     180
gatgatgaag atactatgaa ggatgttgaa gaggggactg atgttaagcc ctctgttgaa     240
agntctnatt taagagatgt tgcaaaagcc attgataatc aagaaccaga agtggat        297

<210> SEQ ID NO 57
<211> LENGTH: 29
<212> TYPE: DNA
<213> ORGANISM: Artificial Sequence
<220> FEATURE:
<223> OTHER INFORMATION: Primer

<400> SEQUENCE: 57
cagatgaaaa cgatgatgaa ttactcaca                                     29

<210> SEQ ID NO 58
<211> LENGTH: 24
<212> TYPE: DNA

```
<213> ORGANISM: Artificial Sequence
<220> FEATURE:
<223> OTHER INFORMATION: Primer

<400> SEQUENCE: 58
agcatcactt gggctagatt cttg                                              24

<210> SEQ ID NO 59
<211> LENGTH: 17
<212> TYPE: DNA
<213> ORGANISM: Artificial Sequence
<220> FEATURE:
<223> OTHER INFORMATION: Probe

<400> SEQUENCE: 59
aggaggtgaa ggatatg                                                      17

<210> SEQ ID NO 60
<211> LENGTH: 17
<212> TYPE: DNA
<213> ORGANISM: Artificial Sequence
<220> FEATURE:
<223> OTHER INFORMATION: Probe

<400> SEQUENCE: 60
aggaggtgaa tgatatg                                                      17

<210> SEQ ID NO 61
<211> LENGTH: 949
<212> TYPE: DNA
<213> ORGANISM: Lactuca serriola
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (70)..(70)
<223> OTHER INFORMATION: n is a, c, g, or t
<220> FEATURE:
<221> NAME/KEY: misc_feature
<222> LOCATION: (85)..(85)
<223> OTHER INFORMATION: n is a, c, g, or t
<220> FEATURE:
<221> NAME/KEY: misc_feature
<222> LOCATION: (127)..(127)
<223> OTHER INFORMATION: n is a, c, g, or t
<220> FEATURE:
<221> NAME/KEY: misc_feature
<222> LOCATION: (147)..(147)
<223> OTHER INFORMATION: n is a, c, g, or t
<220> FEATURE:
<221> NAME/KEY: misc_feature
<222> LOCATION: (406)..(406)
<223> OTHER INFORMATION: n is a, c, g, or t
<220> FEATURE:
<221> NAME/KEY: misc_feature
<222> LOCATION: (466)..(466)
<223> OTHER INFORMATION: n is a, c, g, or t
<220> FEATURE:
<221> NAME/KEY: misc_feature
<222> LOCATION: (549)..(549)
<223> OTHER INFORMATION: n is a, c, g, or t
<220> FEATURE:
<221> NAME/KEY: misc_feature
<222> LOCATION: (869)..(869)
<223> OTHER INFORMATION: n is a, c, g, or t
<220> FEATURE:
<221> NAME/KEY: misc_feature
```

```
<222> LOCATION: (886)..(886)
<223> OTHER INFORMATION: n is a, c, g, or t

<400> SEQUENCE: 61 cgcggggaa tggcttgant atgatgaaac ggacggcnat tcacgatatt gaatactttt      60
gtacccatcn gaacctgccg gaaanaatgc accacttatc atcatcgtcg tggatgctcc    120
gccgctnttg ctgtcatgca acgcctncct tttcgccccc taccgccgtt ttatctactt    180
ctgctgctac tctcactcct cccaagaaga aaaaactcgt tttcatgggt tctccctcgg    240
taatctctcg cccaatgttc ctacaattta cgttaagcat cgccatgggc aataattttc    300
gattggggct tcgattttga aatctgattc gtgttaggtc tcggcttccg ttctcgagac    360
tcttcttgac gcatcctccg ccgctgattc cttattcgag gttgcngcga ttgttaccca    420
gccaccttca ggaagagata ggggaagaaa agtgatgcca tcaccngtag cacaacatgc    480
tctcgataga ggcttcccta atgacctaat tttcacacct gttaaagcca atgaggaagc    540 attttttgtnc aatttcagag cacttgagcc tcaactttgc atcacagcag catatggcaa    600
catattacca accaaatttt taaagattcc tttattaggg actgtgaata tacacccaag    660
cttgttgcct ttataccgtg gagctgctcc tgttcaaaga gcattgcagg atggagttac    720
agaaactggt gtatcattag cattcactat ccgggcatta gatgcgggcc ccattattgc    780
ctatgaaaaa aatgaaaatc gatgatcata ttaaggctcc agaattgctt gatctactat    840
ttgcacaagg atctaaactc ttgcttcana aacttcctct atattnaatg gatctgcaaa    900
gacaaatgct caagaacaag atgactcaaa agccactttg gctccaaaa                949

<210> SEQ ID NO 62
<211> LENGTH: 24
<212> TYPE: DNA
<213> ORGANISM: Artificial Sequence
<220> FEATURE:
<223> OTHER INFORMATION: Primer

<400> SEQUENCE: 62
cgccatgggc aataattttc gatt                                            24

<210> SEQ ID NO 63
<211> LENGTH: 22
<212> TYPE: DNA
<213> ORGANISM: Artificial Sequence
<220> FEATURE:
<223> OTHER INFORMATION: Primer

<400> SEQUENCE: 63
gcgtcaagaa gagtctcgag aa                                              22

<210> SEQ ID NO 64
<211> LENGTH: 16
<212> TYPE: DNA
<213> ORGANISM: Artificial Sequence
<220> FEATURE:
<223> OTHER INFORMATION: Probe

<400> SEQUENCE: 64
taggtctcgg cttccg                                                     16

<210> SEQ ID NO 65
<211> LENGTH: 17
<212> TYPE: DNA
<213> ORGANISM: Artificial Sequence
<220> FEATURE:
```

<223> OTHER INFORMATION: Probe

<400> SEQUENCE: 65
ttaggtctct gcttccg                                                      17

<210> SEQ ID NO 66
<211> LENGTH: 201
<212> TYPE: DNA
<213> ORGANISM: Lactuca serriola

<400> SEQUENCE: 66 cttttactg ttttatcagg aattaaktttt ttttagtaac tatacccatt ccctgagtgt        60
ttgactacct attcttacct aacctatact acgtcgtgtg caggattaca tgcctagttt       120
tttgatggtc catagtttca ttgataacaa ttataagttc aatattgatt ataaattatg       180
catcatgttt ttggcattgt t                                                 201

<210> SEQ ID NO 67
<211> LENGTH: 201
<212> TYPE: DNA
<213> ORGANISM: Lactuca serriola

<400> SEQUENCE: 67
atattgggat tggttcgttg aaatcgattt gaaaaatcag aaaaaattga tttgttctac        60
tagttgtagg aaacttgatt ttttgtaacc tagtgtgacc ttttttttgcc cctattgctt      120 tgtatagaca cttttaggt agatttaac acaacactca aaatgttctc taatataata        180
tcatattatc ggatattttc a                                                 201

<210> SEQ ID NO 68
<211> LENGTH: 201
<212> TYPE: DNA
<213> ORGANISM: Lactuca serriola

<400> SEQUENCE: 68
atgattatgt tggtttctaa ctcaaatcca tcatcccatg gtagatttga tgttggaatt       60
tctaaatctc cacaaactct agattttcta atgataatga taatgtgata atctaactct       120
tatatgattc cattaccact aaggaatgta tgattgcaaa tccttcttag aagagcacaa       180
ttcaaacaat ggtagaatcc t                                                 201

<210> SEQ ID NO 69
<211> LENGTH: 121
<212> TYPE: DNA
<213> ORGANISM: Lactuca serriola
<220> FEATURE:
<221> NAME/KEY: misc_feature
<222> LOCATION: (85)..(85)
<223> OTHER INFORMATION: n is a, c, g, or t
<220> FEATURE:
<221> NAME/KEY: misc_feature
<222> LOCATION: (103)..(103)
<223> OTHER INFORMATION: n is a, c, g, or t

<400> SEQUENCE: 69
agcaagcatc gccgtcatca atcctccggt acttgttccg gcgatgacat caaagtaatc       60
tgcaattcgt gcctcaggtc catcnatttc ctgaagcttg gantcgagaa atgaaagtat      120
g                                                                      121

<210> SEQ ID NO 70
<211> LENGTH: 121

```
<212> TYPE: DNA
<213> ORGANISM: Lactuca serriola

<400> SEQUENCE: 70
ttccagttct agttccagtt ccatcaattt caaaggaatt atggtgggaa atgcagtgac      60
agattattac tatgacaacc ttggaactgt gacatattgg tggagtcacg ctatgatatc     120
t                                                                     121

<210> SEQ ID NO 71
<211> LENGTH: 27
<212> TYPE: DNA
<213> ORGANISM: Artificial Sequence
<220> FEATURE:
<223> OTHER INFORMATION: Primer

<400> SEQUENCE: 71
agttccagtt ccatcaattt caaagga                                          27

<210> SEQ ID NO 72
<211> LENGTH: 25
<212> TYPE: DNA
<213> ORGANISM: Artificial Sequence
<220> FEATURE:
<223> OTHER INFORMATION: Primer

<400> SEQUENCE: 72
gtcacagttc caaggttgtc atagt                                            25

<210> SEQ ID NO 73
<211> LENGTH: 17
<212> TYPE: DNA
<213> ORGANISM: Artificial Sequence
<220> FEATURE:
<223> OTHER INFORMATION: Probe

<400> SEQUENCE: 73
tgcagtgaca gattatt                                                     17

<210> SEQ ID NO 74
<211> LENGTH: 15
<212> TYPE: DNA
<213> ORGANISM: Artificial Sequence
<220> FEATURE:
<223> OTHER INFORMATION: Probe

<400> SEQUENCE: 74
cagtgacgga ttatt                                                       15

<210> SEQ ID NO 75
<211> LENGTH: 201
<212> TYPE: DNA
<213> ORGANISM: Lactuca serriola

<400> SEQUENCE: 75
cattggcatt agagatggta gtgaaataac tatcatctca aatcatcaca ctgtatgttg      60
acatttacta ttttgtatgt tgacatgtgt atagaatgat attttggtat gttctgttca     120
taggatctta tggaagtagt ttaataaaga gtttcacatg ctaagcatag acaatatgac     180
aggtcaacca ttaggtgttt c                                                201

<210> SEQ ID NO 76
<211> LENGTH: 121
<212> TYPE: DNA
```

<213> ORGANISM: Lactuca serriola
<220> FEATURE:
<221> NAME/KEY: misc_feature
<222> LOCATION: (114)..(114)
<223> OTHER INFORMATION: n is a, c, g, or t

<400> SEQUENCE: 76
cgacattaca gccgcatcaa acgataacat tcgcgattct tgaagcccgt gattcacttc    60
tggactattc gcaatctttg aagtcggttt aggagacgat aaattcttgt tttngtttcg   120
a                                                                   121

<210> SEQ ID NO 77
<211> LENGTH: 25
<212> TYPE: DNA
<213> ORGANISM: Artificial Sequence
<220> FEATURE:
<223> OTHER INFORMATION: Primer

<400> SEQUENCE: 77
gcatcaaacg ataacattcg cgatt                                          25

<210> SEQ ID NO 78
<211> LENGTH: 25
<212> TYPE: DNA
<213> ORGANISM: Artificial Sequence
<220> FEATURE:
<223> OTHER INFORMATION: Primer

<400> SEQUENCE: 78
cgtctcctaa accgacttca aagat                                          25

<210> SEQ ID NO 79
<211> LENGTH: 20
<212> TYPE: DNA
<213> ORGANISM: Artificial Sequence
<220> FEATURE:
<223> OTHER INFORMATION: Probe

<400> SEQUENCE: 79
tgattcactt ctggactatt                                                20

<210> SEQ ID NO 80
<211> LENGTH: 17
<212> TYPE: DNA
<213> ORGANISM: Artificial Sequence
<220> FEATURE:
<223> OTHER INFORMATION: Probe

<400> SEQUENCE: 80
ttcacttccg gactatt                                                   17

<210> SEQ ID NO 81
<211> LENGTH: 121
<212> TYPE: DNA
<213> ORGANISM: Lactuca serriola

<400> SEQUENCE: 81
tttcacgtct gctgcatctg ttgctaacct cgctgccact agactcgagt tatgctcctc    60
ttcatcaaac cacccaactt catttctcat tatcgctgaa agcatcattc ttcgaactcg   120
t                                                                   121

<210> SEQ ID NO 82
<211> LENGTH: 19

```
<212> TYPE: DNA
<213> ORGANISM: Artificial Sequence
<220> FEATURE:
<223> OTHER INFORMATION: Primer

<400> SEQUENCE: 82
acctcgctgc cactagact                                                     19

<210> SEQ ID NO 83
<211> LENGTH: 27
<212> TYPE: DNA
<213> ORGANISM: Artificial Sequence
<220> FEATURE:
<223> OTHER INFORMATION: Primer

<400> SEQUENCE: 83
agaatgatgc tttcagcgat aatgaga                                            27

<210> SEQ ID NO 84
<211> LENGTH: 20
<212> TYPE: DNA
<213> ORGANISM: Artificial Sequence
<220> FEATURE:
<223> OTHER INFORMATION: Probe

<400> SEQUENCE: 84
agttatgctc ctcttcatca                                                    20

<210> SEQ ID NO 85
<211> LENGTH: 20
<212> TYPE: DNA
<213> ORGANISM: Artificial Sequence
<220> FEATURE:
<223> OTHER INFORMATION: Probe

<400> SEQUENCE: 85
agttatgctc ctcctcatca                                                    20

<210> SEQ ID NO 86
<211> LENGTH: 870
<212> TYPE: DNA
<213> ORGANISM: Lactuca serriola
<220> FEATURE:
<221> NAME/KEY: misc_feature
<222> LOCATION: (148)..(148)
<223> OTHER INFORMATION: n is a, c, g, or t
<220> FEATURE:
<221> NAME/KEY: misc_feature
<222> LOCATION: (157)..(157)
<223> OTHER INFORMATION: n is a, c, g, or t
<220> FEATURE:
<221> NAME/KEY: misc_feature
<222> LOCATION: (270)..(270)
<223> OTHER INFORMATION: n is a, c, g, or t
<220> FEATURE:
<221> NAME/KEY: misc_feature
<222> LOCATION: (327)..(327)
<223> OTHER INFORMATION: n is a, c, g, or t
<220> FEATURE:
<221> NAME/KEY: misc_feature
<222> LOCATION: (394)..(394)
<223> OTHER INFORMATION: n is a, c, g, or t
<220> FEATURE:
<221> NAME/KEY: misc_feature
<222> LOCATION: (425)..(425)
<223> OTHER INFORMATION: n is a, c, g, or t
<220> FEATURE:
<221> NAME/KEY: misc_feature
<222> LOCATION: (572)..(572)
<223> OTHER INFORMATION: n is a, c, g, or t
<220> FEATURE:
```

```
<221> NAME/KEY: misc_feature
<222> LOCATION: (601)..(601)
<223> OTHER INFORMATION: n is a, c, g, or t
<220> FEATURE:
<221> NAME/KEY: misc_feature
<222> LOCATION: (658)..(658)
<223> OTHER INFORMATION: n is a, c, g, or t
<220> FEATURE:
<221> NAME/KEY: misc_feature
<222> LOCATION: (723)..(723)
<223> OTHER INFORMATION: n is a, c, g, or t
<220> FEATURE:
<221> NAME/KEY: misc_feature
<222> LOCATION: (725)..(725)
<223> OTHER INFORMATION: n is a, c, g, or t
<220> FEATURE:
<221> NAME/KEY: misc_feature
<222> LOCATION: (747)..(747)
<223> OTHER INFORMATION: n is a, c, g, or t

<400> SEQUENCE: 86
ggaaaaacgg aaggacatag agttagagtg ggagtttaga agcagaagga agctatggcg      60
tcagtgagag ttgactcgga ggtgactcgg ataatgatcg gtgtgaacga gtcaagcatc     120
aaaggatatc cacatgcttc aattagtngc aaatcancat ttgaatggac tctgaacaag     180
atcattcgct ccaatacctc cggttttaag ctccttttc tccatgttca agttcctgat     240
gaagacggtt tgatgatgt tgatagtatn tacgcctcac cacaagattt tagagatgca     300
aatcgtaaag acaagattaa tggatcncat ttgctggagt actttgtgaa cagatgtcat     360
gatatagggg ttgtttgtga agcatgggtg aagngggtg atgccaaaga agtaatctgc     420
catgnggtca aaagagtcaa accagacctc cttgtagttg gaaacagagg tcttggaccc     480
ttccagaggg tatttgtggg aactgtgagt gaattctgtg tgaagcactg tgaatgccca     540
gttgtaacaa tcaaacgcag tgcagaagag anccctaatg atcctgtaga tgattgattg     600
ntcctctaaa agctactatt aataatgtaa aatcttctct acaaccctct ttcctggntt     660
gtcttttta atggagattt agctgtgtgt atctgtaaga cctatgagtt ccttttttct     720
agntnagttg ttatacaact atgttncaa ggctgctttt gtgatatgta actagattga     780
caagcttttt agggatgaaa tcacatttat gtcttttcta ctctctaaca ttacatcaaa     840
aaatatattc cttatatact cttgacaaaa                                    870

<210> SEQ ID NO 87
<211> LENGTH: 24
<212> TYPE: DNA
<213> ORGANISM: Artificial Sequence
<220> FEATURE:
<223> OTHER INFORMATION: Primer

<400> SEQUENCE: 87
tgtgagtgaa ttctgtgtga agca                                            24

<210> SEQ ID NO 88
<211> LENGTH: 23
<212> TYPE: DNA
<213> ORGANISM: Artificial Sequence
<220> FEATURE:
<223> OTHER INFORMATION: Primer

<400> SEQUENCE: 88
cttctgcact gcgtttgatt gtt                                             23

<210> SEQ ID NO 89
<211> LENGTH: 15
```

```
<212> TYPE: DNA
<213> ORGANISM: Artificial Sequence
<220> FEATURE:
<223> OTHER INFORMATION: Probe

<400> SEQUENCE: 89
caactgggca ttcac                                                              15

<210> SEQ ID NO 90
<211> LENGTH: 16
<212> TYPE: DNA
<213> ORGANISM: Artificial Sequence
<220> FEATURE:
<223> OTHER INFORMATION: Probe

<400> SEQUENCE: 90
acaactggac attcac                                                             16

<210> SEQ ID NO 91
<211> LENGTH: 1917
<212> TYPE: DNA
<213> ORGANISM: Lactuca serriola
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (182)..(182)
<223> OTHER INFORMATION: n is a, c, g, or t
<220> FEATURE:
<221> NAME/KEY: misc_feature
<222> LOCATION: (262)..(262)
<223> OTHER INFORMATION: n is a, c, g, or t
<220> FEATURE:
<221> NAME/KEY: misc_feature
<222> LOCATION: (268)..(268)
<223> OTHER INFORMATION: n is a, c, g, or t
<220> FEATURE:
<221> NAME/KEY: misc_feature
<222> LOCATION: (275)..(275)
<223> OTHER INFORMATION: n is a, c, g, or t
<220> FEATURE:
<221> NAME/KEY: misc_feature
<222> LOCATION: (304)..(304)
<223> OTHER INFORMATION: n is a, c, g, or t
<220> FEATURE:
<221> NAME/KEY: misc_feature
<222> LOCATION: (356)..(356)
<223> OTHER INFORMATION: n is a, c, g, or t
<220> FEATURE:
<221> NAME/KEY: misc_feature
<222> LOCATION: (360)..(360)
<223> OTHER INFORMATION: n is a, c, g, or t
<220> FEATURE:
<221> NAME/KEY: misc_feature
<222> LOCATION: (391)..(391)
<223> OTHER INFORMATION: n is a, c, g, or t
<220> FEATURE:
<221> NAME/KEY: misc_feature
<222> LOCATION: (535)..(535)
<223> OTHER INFORMATION: n is a, c, g, or t
<220> FEATURE:
<221> NAME/KEY: misc_feature
<222> LOCATION: (603)..(603)
<223> OTHER INFORMATION: n is a, c, g, or t
<220> FEATURE:
<221> NAME/KEY: misc_feature
<222> LOCATION: (620)..(620)
<223> OTHER INFORMATION: n is a, c, g, or t
<220> FEATURE:
```

```
<221> NAME/KEY: misc_feature
<222> LOCATION: (627)..(627)
<223> OTHER INFORMATION: n is a, c, g, or t
<220> FEATURE:
<221> NAME/KEY: misc_feature
<222> LOCATION: (632)..(632)
<223> OTHER INFORMATION: n is a, c, g, or t
<220> FEATURE:
<221> NAME/KEY: misc_feature
<222> LOCATION: (636)..(636)
<223> OTHER INFORMATION: n is a, c, g, or t
<220> FEATURE:
<221> NAME/KEY: misc_feature
<222> LOCATION: (670)..(670)
<223> OTHER INFORMATION: n is a, c, g, or t
<220> FEATURE:
<221> NAME/KEY: misc_feature
<222> LOCATION: (695)..(695)
<223> OTHER INFORMATION: n is a, c, g, or t
<220> FEATURE:
<221> NAME/KEY: misc_feature
<222> LOCATION: (716)..(716)
<223> OTHER INFORMATION: n is a, c, g, or t
<220> FEATURE:
<221> NAME/KEY: misc_feature
<222> LOCATION: (735)..(735)
<223> OTHER INFORMATION: n is a, c, g, or t
<220> FEATURE:
<221> NAME/KEY: misc_feature
<222> LOCATION: (765)..(765)
<223> OTHER INFORMATION: n is a, c, g, or t
<220> FEATURE:
<221> NAME/KEY: misc_feature
<222> LOCATION: (837)..(837)
<223> OTHER INFORMATION: n is a, c, g, or t
<220> FEATURE:
<221> NAME/KEY: misc_feature
<222> LOCATION: (840)..(840)
<223> OTHER INFORMATION: n is a, c, g, or t
<220> FEATURE:
<221> NAME/KEY: misc_feature
<222> LOCATION: (882)..(882)
<223> OTHER INFORMATION: n is a, c, g, or t
<220> FEATURE:
<221> NAME/KEY: misc_feature
<222> LOCATION: (914)..(914)
<223> OTHER INFORMATION: n is a, c, g, or t
<220> FEATURE:
<221> NAME/KEY: misc_feature
<222> LOCATION: (926)..(926)
<223> OTHER INFORMATION: n is a, c, g, or t
<220> FEATURE:
<221> NAME/KEY: misc_feature
<222> LOCATION: (929)..(929)
<223> OTHER INFORMATION: n is a, c, g, or t
<220> FEATURE:
<221> NAME/KEY: misc_feature
<222> LOCATION: (947)..(947)
<223> OTHER INFORMATION: n is a, c, g, or t
<220> FEATURE:
<221> NAME/KEY: misc_feature
<222> LOCATION: (1101)..(1101)
<223> OTHER INFORMATION: n is a, c, g, or t
<220> FEATURE:
<221> NAME/KEY: misc_feature
<222> LOCATION: (1104)..(1104)
<223> OTHER INFORMATION: n is a, c, g, or t
<220> FEATURE:
<221> NAME/KEY: misc_feature
<222> LOCATION: (1109)..(1109)
<223> OTHER INFORMATION: n is a, c, g, or t
<220> FEATURE:
<221> NAME/KEY: misc_feature
<222> LOCATION: (1111)..(1111)
<223> OTHER INFORMATION: n is a, c, g, or t
<220> FEATURE:
<221> NAME/KEY: misc_feature
<222> LOCATION: (1116)..(1116)
<223> OTHER INFORMATION: n is a, c, g, or t
```

-continued

```
<220> FEATURE:
<221> NAME/KEY: misc_feature
<222> LOCATION: (1124)..(1124)
<223> OTHER INFORMATION: n is a, c, g, or t
<220> FEATURE:
<221> NAME/KEY: misc_feature
<222> LOCATION: (1153)..(1153)
<223> OTHER INFORMATION: n is a, c, g, or t
<220> FEATURE:
<221> NAME/KEY: misc_feature
<222> LOCATION: (1215)..(1215)
<223> OTHER INFORMATION: n is a, c, g, or t
<220> FEATURE:
<221> NAME/KEY: misc_feature
<222> LOCATION: (1221)..(1221)
<223> OTHER INFORMATION: n is a, c, g, or t
<220> FEATURE:
<221> NAME/KEY: misc_feature
<222> LOCATION: (1227)..(1227)
<223> OTHER INFORMATION: n is a, c, g, or t
<220> FEATURE:
<221> NAME/KEY: misc_feature
<222> LOCATION: (1241)..(1241)
<223> OTHER INFORMATION: n is a, c, g, or t
<220> FEATURE:
<221> NAME/KEY: misc_feature
<222> LOCATION: (1246)..(1246)
<223> OTHER INFORMATION: n is a, c, g, or t
<220> FEATURE:
<221> NAME/KEY: misc_feature
<222> LOCATION: (1251)..(1251)
<223> OTHER INFORMATION: n is a, c, g, or t
<220> FEATURE:
<221> NAME/KEY: misc_feature
<222> LOCATION: (1284)..(1284)
<223> OTHER INFORMATION: n is a, c, g, or t
<220> FEATURE:
<221> NAME/KEY: misc_feature
<222> LOCATION: (1291)..(1291)
<223> OTHER INFORMATION: n is a, c, g, or t
<220> FEATURE:
<221> NAME/KEY: misc_feature
<222> LOCATION: (1297)..(1297)
<223> OTHER INFORMATION: n is a, c, g, or t
<220> FEATURE:
<221> NAME/KEY: misc_feature
<222> LOCATION: (1305)..(1305)
<223> OTHER INFORMATION: n is a, c, g, or t
<220> FEATURE:
<221> NAME/KEY: misc_feature
<222> LOCATION: (1318)..(1318)
<223> OTHER INFORMATION: n is a, c, g, or t
<220> FEATURE:
<221> NAME/KEY: misc_feature
<222> LOCATION: (1321)..(1321)
<223> OTHER INFORMATION: n is a, c, g, or t
<220> FEATURE:
<221> NAME/KEY: misc_feature
<222> LOCATION: (1346)..(1346)
<223> OTHER INFORMATION: n is a, c, g, or t
<220> FEATURE:
<221> NAME/KEY: misc_feature
<222> LOCATION: (1348)..(1348)
<223> OTHER INFORMATION: n is a, c, g, or t
<220> FEATURE:
<221> NAME/KEY: misc_feature
<222> LOCATION: (1350)..(1350)
<223> OTHER INFORMATION: n is a, c, g, or t
<220> FEATURE:
<221> NAME/KEY: misc_feature
<222> LOCATION: (1366)..(1366)
<223> OTHER INFORMATION: n is a, c, g, or t
<220> FEATURE:
<221> NAME/KEY: misc_feature
<222> LOCATION: (1395)..(1395)
<223> OTHER INFORMATION: n is a, c, g, or t
<220> FEATURE:
<221> NAME/KEY: misc_feature
<222> LOCATION: (1400)..(1400)
```

```
<223> OTHER INFORMATION: n is a, c, g, or t
<220> FEATURE:
<221> NAME/KEY: misc_feature
<222> LOCATION: (1405)..(1405)
<223> OTHER INFORMATION: n is a, c, g, or t
<220> FEATURE:
<221> NAME/KEY: misc_feature
<222> LOCATION: (1407)..(1407)
<223> OTHER INFORMATION: n is a, c, g, or t
<220> FEATURE:
<221> NAME/KEY: misc_feature
<222> LOCATION: (1413)..(1413)
<223> OTHER INFORMATION: n is a, c, g, or t
<220> FEATURE:
<221> NAME/KEY: misc_feature
<222> LOCATION: (1419)..(1419)
<223> OTHER INFORMATION: n is a, c, g, or t
<220> FEATURE:
<221> NAME/KEY: misc_feature
<222> LOCATION: (1432)..(1432)
<223> OTHER INFORMATION: n is a, c, g, or t
<220> FEATURE:
<221> NAME/KEY: misc_feature
<222> LOCATION: (1444)..(1444)
<223> OTHER INFORMATION: n is a, c, g, or t
<220> FEATURE:
<221> NAME/KEY: misc_feature
<222> LOCATION: (1447)..(1447)
<223> OTHER INFORMATION: n is a, c, g, or t
<220> FEATURE:
<221> NAME/KEY: misc_feature
<222> LOCATION: (1477)..(1477)
<223> OTHER INFORMATION: n is a, c, g, or t
<220> FEATURE:
<221> NAME/KEY: misc_feature
<222> LOCATION: (1497)..(1497)
<223> OTHER INFORMATION: n is a, c, g, or t
<220> FEATURE:
<221> NAME/KEY: misc_feature
<222> LOCATION: (1502)..(1502)
<223> OTHER INFORMATION: n is a, c, g, or t
<220> FEATURE:
<221> NAME/KEY: misc_feature
<222> LOCATION: (1512)..(1512)
<223> OTHER INFORMATION: n is a, c, g, or t
<220> FEATURE:
<221> NAME/KEY: misc_feature
<222> LOCATION: (1515)..(1515)
<223> OTHER INFORMATION: n is a, c, g, or t
<220> FEATURE:
<221> NAME/KEY: misc_feature
<222> LOCATION: (1521)..(1521)
<223> OTHER INFORMATION: n is a, c, g, or t
<220> FEATURE:
<221> NAME/KEY: misc_feature
<222> LOCATION: (1527)..(1527)
<223> OTHER INFORMATION: n is a, c, g, or t
<220> FEATURE:
<221> NAME/KEY: misc_feature
<222> LOCATION: (1530)..(1530)
<223> OTHER INFORMATION: n is a, c, g, or t
<220> FEATURE:
<221> NAME/KEY: misc_feature
<222> LOCATION: (1545)..(1545)
<223> OTHER INFORMATION: n is a, c, g, or t
<220> FEATURE:
<221> NAME/KEY: misc_feature
<222> LOCATION: (1558)..(1558)
<223> OTHER INFORMATION: n is a, c, g, or t
<220> FEATURE:
<221> NAME/KEY: misc_feature
<222> LOCATION: (1584)..(1584)
<223> OTHER INFORMATION: n is a, c, g, or t
<220> FEATURE:
<221> NAME/KEY: misc_feature
<222> LOCATION: (1591)..(1591)
<223> OTHER INFORMATION: n is a, c, g, or t
<220> FEATURE:
<221> NAME/KEY: misc_feature
```

```
<222> LOCATION: (1593)..(1593)
<223> OTHER INFORMATION: n is a, c, g, or t
<220> FEATURE:
<221> NAME/KEY: misc_feature
<222> LOCATION: (1601)..(1601)
<223> OTHER INFORMATION: n is a, c, g, or t
<220> FEATURE:
<221> NAME/KEY: misc_feature
<222> LOCATION: (1612)..(1612)
<223> OTHER INFORMATION: n is a, c, g, or t
<220> FEATURE:
<221> NAME/KEY: misc_feature
<222> LOCATION: (1614)..(1614)
<223> OTHER INFORMATION: n is a, c, g, or t
<220> FEATURE:
<221> NAME/KEY: misc_feature
<222> LOCATION: (1621)..(1621)
<223> OTHER INFORMATION: n is a, c, g, or t
<220> FEATURE:
<221> NAME/KEY: misc_feature
<222> LOCATION: (1625)..(1625)
<223> OTHER INFORMATION: n is a, c, g, or t
<220> FEATURE:
<221> NAME/KEY: misc_feature
<222> LOCATION: (1627)..(1627)
<223> OTHER INFORMATION: n is a, c, g, or t
<220> FEATURE:
<221> NAME/KEY: misc_feature
<222> LOCATION: (1636)..(1636)
<223> OTHER INFORMATION: n is a, c, g, or t
<220> FEATURE:
<221> NAME/KEY: misc_feature
<222> LOCATION: (1644)..(1644)
<223> OTHER INFORMATION: n is a, c, g, or t
<220> FEATURE:
<221> NAME/KEY: misc_feature
<222> LOCATION: (1661)..(1661)
<223> OTHER INFORMATION: n is a, c, g, or t
<220> FEATURE:
<221> NAME/KEY: misc_feature
<222> LOCATION: (1666)..(1666)
<223> OTHER INFORMATION: n is a, c, g, or t
<220> FEATURE:
<221> NAME/KEY: misc_feature
<222> LOCATION: (1682)..(1682)
<223> OTHER INFORMATION: n is a, c, g, or t
<220> FEATURE:
<221> NAME/KEY: misc_feature
<222> LOCATION: (1689)..(1689)
<223> OTHER INFORMATION: n is a, c, g, or t
<220> FEATURE:
<221> NAME/KEY: misc_feature
<222> LOCATION: (1698)..(1698)
<223> OTHER INFORMATION: n is a, c, g, or t
<220> FEATURE:
<221> NAME/KEY: misc_feature
<222> LOCATION: (1701)..(1701)
<223> OTHER INFORMATION: n is a, c, g, or t
<220> FEATURE:
<221> NAME/KEY: misc_feature
<222> LOCATION: (1706)..(1706)
<223> OTHER INFORMATION: n is a, c, g, or t
<220> FEATURE:
<221> NAME/KEY: misc_feature
<222> LOCATION: (1716)..(1716)
<223> OTHER INFORMATION: n is a, c, g, or t
<220> FEATURE:
<221> NAME/KEY: misc_feature
<222> LOCATION: (1729)..(1729)
<223> OTHER INFORMATION: n is a, c, g, or t
<220> FEATURE:
<221> NAME/KEY: misc_feature
<222> LOCATION: (1735)..(1735)
<223> OTHER INFORMATION: n is a, c, g, or t
<220> FEATURE:
<221> NAME/KEY: misc_feature
<222> LOCATION: (1742)..(1742)
<223> OTHER INFORMATION: n is a, c, g, or t
<220> FEATURE:
```

```
<221> NAME/KEY: misc_feature
<222> LOCATION: (1747)..(1747)
<223> OTHER INFORMATION: n is a, c, g, or t
<220> FEATURE:
<221> NAME/KEY: misc_feature
<222> LOCATION: (1753)..(1753)
<223> OTHER INFORMATION: n is a, c, g, or t
<220> FEATURE:
<221> NAME/KEY: misc_feature
<222> LOCATION: (1755)..(1755)
<223> OTHER INFORMATION: n is a, c, g, or t
<220> FEATURE:
<221> NAME/KEY: misc_feature
<222> LOCATION: (1758)..(1758)
<223> OTHER INFORMATION: n is a, c, g, or t
<220> FEATURE:
<221> NAME/KEY: misc_feature
<222> LOCATION: (1765)..(1765)
<223> OTHER INFORMATION: n is a, c, g, or t
<220> FEATURE:
<221> NAME/KEY: misc_feature
<222> LOCATION: (1768)..(1768)
<223> OTHER INFORMATION: n is a, c, g, or t
<220> FEATURE:
<221> NAME/KEY: misc_feature
<222> LOCATION: (1775)..(1775)
<223> OTHER INFORMATION: n is a, c, g, or t
<220> FEATURE:
<221> NAME/KEY: misc_feature
<222> LOCATION: (1777)..(1777)
<223> OTHER INFORMATION: n is a, c, g, or t
<220> FEATURE:
<221> NAME/KEY: misc_feature
<222> LOCATION: (1784)..(1784)
<223> OTHER INFORMATION: n is a, c, g, or t
<220> FEATURE:
<221> NAME/KEY: misc_feature
<222> LOCATION: (1786)..(1786)
<223> OTHER INFORMATION: n is a, c, g, or t
<220> FEATURE:
<221> NAME/KEY: misc_feature
<222> LOCATION: (1791)..(1791)
<223> OTHER INFORMATION: n is a, c, g, or t
<220> FEATURE:
<221> NAME/KEY: misc_feature
<222> LOCATION: (1807)..(1807)
<223> OTHER INFORMATION: n is a, c, g, or t
<220> FEATURE:
<221> NAME/KEY: misc_feature
<222> LOCATION: (1818)..(1818)
<223> OTHER INFORMATION: n is a, c, g, or t
<220> FEATURE:
<221> NAME/KEY: misc_feature
<222> LOCATION: (1821)..(1821)
<223> OTHER INFORMATION: n is a, c, g, or t
<220> FEATURE:
<221> NAME/KEY: misc_feature
<222> LOCATION: (1828)..(1828)
<223> OTHER INFORMATION: n is a, c, g, or t
<220> FEATURE:
<221> NAME/KEY: misc_feature
<222> LOCATION: (1830)..(1830)
<223> OTHER INFORMATION: n is a, c, g, or t
<220> FEATURE:
<221> NAME/KEY: misc_feature
<222> LOCATION: (1837)..(1837)
<223> OTHER INFORMATION: n is a, c, g, or t
<220> FEATURE:
<221> NAME/KEY: misc_feature
<222> LOCATION: (1847)..(1847)
<223> OTHER INFORMATION: n is a, c, g, or t
<220> FEATURE:
<221> NAME/KEY: misc_feature
<222> LOCATION: (1850)..(1850)
<223> OTHER INFORMATION: n is a, c, g, or t
<220> FEATURE:
<221> NAME/KEY: misc_feature
<222> LOCATION: (1914)..(1914)
<223> OTHER INFORMATION: n is a, c, g, or t
```

<400> SEQUENCE: 91

```
gcgggggcg acgatttngg gggncaagtt gatttcctta tactttactt caaaatcttc      60
tccatagttg aattgctgat aatcagttca gaagcttgtt tgctgcattt cctggtgtat    120
ggcaccaatg aagggcattc tttctctgca aagggctgtt ctatcaaggc atcaaaatgc    180
anactggggg ataaatgcta ccggctagac ttttcagcac gcagtctgcg acaaccgcca    240
ccaccgccca accaccaccg cnaccacntc caccngaaaa aacccacttt ggtggcctga    300
aagntgaaga ccgcatcttc acaaacctat acggtttaca cgaccccttt ctcaanggcn    360
caatgaaacg tggcgattgg catagaacta nagacatagt aatcaaaggt gctgattgga    420
tagtaaacga aatgaaaaaa tccggcttac gtggacgtgg aggtgctggt ttcccatcag    480
ggctaaaatg gtcattcatg ccaaaagtat ccgatggtcg tccatcttat cttgntgtaa    540
acgcagacga aagtgaaccc ggaacttgca agatagaga aatcatgcgt aacgatccac    600
acnagcttct agaaggatgn ttaatanctg gngtangtat gcgtgcaacc gctgcctaca    660
tttacatcan gggcgaatac gtaaatgaac gtttnaattt agaaaaagca agaaangaag    720
catatgcagc tggantactt ggaaaaaacg cgtgtgggtc cgggnatgat ttcgatgtcc    780
atatccattt cggagccgga gcctacattt gtggtgaaga aaccgcgctt ctcgaanccn    840
tcgagggcaa acaaggaaaa ccgcgtttga agccgccttt tnccgccaac gcggggttat    900
acgggtgtcc cacnaccgtc acaaangtng aaacaatcgc ggtgtcnccg actattctaa    960
gacgtgggcc cgagtggttt tctagctttg gtagaaagaa cattcgggga ctaaacttt   1020
ctgtatatcg ggtcatgtga acaaaccgtg tacagtggaa gaggagatga gtattccatt   1080
gaaggagttg ttggagcggc nttntggcng nttgangggc gganggggaca atttgctagc   1140
ggtgattccg ggnggttctt ctgttccttt gcttacaaag gatttatgcg aagacgtgtt   1200
gatggatttt gatgngttga nagctgntca atctggatta nggacngctg ntgttattgt   1260
gatggataag tcgactgata ttgnggatgc nattgcnagg ctttngtatt tttataanca   1320
ngagagttgt ggtcagtgta cgcctngnan ggagggaact gggtgncttt ggatgattat   1380
ggaaaggatg aaagntgggn atgcnanatt ggnggagant gatatgcttc angaagtgac   1440
taancanatt gaagggcata ctatttgtgc acttggngat gctgctgctt ggcctgntca   1500
anggcttatt anacntttta ngcctgngan ggagaggagg atcanggagc gtgctgancg   1560
ggagttgctt caagcagctg cttnaaatca ngntgaatgg nttcctacct gnangaaaac   1620
ntgangngac tttggncttt ggancataat atgattaatg nttaangttt gtgttgctgt   1680
tnaactacna tgtgattnaa nacagnaccc ttctcnttag attgggggna acttntgtgt   1740
gnttaangat acnanganat cctantgnta ttatngnact tcantnagcc ntatgctttt   1800
ggacacntgt caaaatgnta ntaagccnan tgcattnttg taatcanacn atggaagctt   1860
ttcataagct caagtttcat gccttgtcag aacattaacc gttggtggtt tggngaa     1917
```

<210> SEQ ID NO 92
<211> LENGTH: 26
<212> TYPE: DNA
<213> ORGANISM: Artificial Sequence
<220> FEATURE:
<223> OTHER INFORMATION: Primer

<400> SEQUENCE: 92

```
aaaggtgctg attggatagt aaacga                                          26
```

```
<210> SEQ ID NO 93
<211> LENGTH: 23
<212> TYPE: DNA
<213> ORGANISM: Artificial Sequence
<220> FEATURE:
<223> OTHER INFORMATION: Primer

<400> SEQUENCE: 93
attttagccc tgatgggaaa cca                                              23

<210> SEQ ID NO 94
<211> LENGTH: 16
<212> TYPE: DNA
<213> ORGANISM: Artificial Sequence
<220> FEATURE:
<223> OTHER INFORMATION: Probe

<400> SEQUENCE: 94
cacgtaagcc ggattt                                                      16

<210> SEQ ID NO 95
<211> LENGTH: 16
<212> TYPE: DNA
<213> ORGANISM: Artificial Sequence
<220> FEATURE:
<223> OTHER INFORMATION: Probe

<400> SEQUENCE: 95
cacgtaagcc agattt                                                      16
```